US007604989B2

(12) United States Patent
Reff et al.

(10) Patent No.: US 7,604,989 B2
(45) Date of Patent: Oct. 20, 2009

(54) INHIBITION OF APOPTOSIS PROCESS AND IMPROVEMENT OF CELL PERFORMANCE

(75) Inventors: Mitchell Reff, San Diego, CA (US); Eric Ailor, San Diego, CA (US); Michael J. Betenbaugh, Baltimore, MD (US); Bruno Figueroa, Jr., Baltimore, MD (US); Marie Hardwick, Baltimore, MD (US)

(73) Assignees: Johns Hopkins University, Baltimore, MD (US); Biogen Idec Inc., San Diego, CA (US)

( * ) Notice: Subject to any disclaimer, the term of this patent is extended or adjusted under 35 U.S.C. 154(b) by 559 days.

(21) Appl. No.: 10/191,052

(22) Filed: Jul. 10, 2002

(65) Prior Publication Data

US 2003/0064510 A1　Apr. 3, 2003

Related U.S. Application Data

(60) Provisional application No. 60/303,813, filed on Jul. 10, 2001.

(51) Int. Cl.
*C12N 5/00* (2006.01)
(52) U.S. Cl. .................................................... 435/325
(58) Field of Classification Search ................. 435/465, 435/4, 325
See application file for complete search history.

(56) References Cited

U.S. PATENT DOCUMENTS

| | | | | |
|---|---|---|---|---|
| 5,550,050 | A | 8/1996 | Holland et al. | ............... 435/240 |
| 5,811,524 | A | 9/1998 | Brams et al. | |
| 5,830,698 | A | 11/1998 | Reff et al. | |
| 5,840,298 | A | 11/1998 | Brams et al. | |
| 5,866,125 | A | 2/1999 | Brams et al. | |
| 5,877,210 | A | 3/1999 | Schieven | .................... 514/492 |
| 5,897,992 | A | 4/1999 | Fearnhead et al. | ............ 435/29 |
| 5,939,068 | A | 8/1999 | Brams et al. | |
| 5,955,364 | A | 9/1999 | Brams et al. | |
| 5,958,765 | A | 9/1999 | Brams et al. | |
| 5,969,102 | A | 10/1999 | Bram et al. | .................. 530/350 |
| 5,998,144 | A | 12/1999 | Reff et al. | |
| 6,001,358 | A | 12/1999 | Black et al. | |
| 6,011,138 | A | 1/2000 | Reff | |
| 6,017,733 | A | 1/2000 | Reff | |
| 6,087,129 | A | 7/2000 | Newgard et al. | ............ 435/69.4 |
| 6,136,310 | A | 10/2000 | Hanna et al. | |
| 6,140,118 | A | 10/2000 | Tsai et al. | .................... 435/325 |
| 6,159,730 | A | 12/2000 | Reff | |
| 6,512,095 | B2 | 1/2003 | Baum | |
| 6,586,206 | B1 | 7/2003 | Dixit et al. | |

FOREIGN PATENT DOCUMENTS

| | | | |
|---|---|---|---|
| EP | 1348758 A1 | 1/2003 | |
| EP | 1468079 A1 | 10/2004 | |
| WO | WO 00/50453 | 8/2000 | |

OTHER PUBLICATIONS

Terada et al. "Anti-apoptotic genes, bag-1 and bcl-2, enabled hybridoma cells to survive under treatment for arresting cell cycle" Cytotechnology, 1997, vol. 25, pp. 17-23.*
Goswani et al. (1999, Biotechnology and Bioengineering 62(6):632-40).*
Terada et al. (1997, Cytotechnology 25:17-23).*
James et al. (2000, Biotechnology and Bioengineering 67(2):134-140).*
Luers et al (2000, Eur. J. Cell Biol 79(9):653-7) (abstract only).*
Mercille (1999, Biotechnol. Bioeng. 63(5):529-43, abstract only).*
Chau et al. (2000, Molecular Cell 6:31-40).*
Goswani et al (1999, Biotechnology and Bioengineering 62(6):632-40).*
Terada et al (1997, Cytotechnology 25:17-23).*
James et al (2000, Biotechnology and Bioengineering 67(2):134-140).*
Chau et al (2000, Molecular Cell 6:31-40).*
Luers et al (2000, Eur. J. Cell Biol 79(9):653-7).*
Figueroa et al (2004, Biotech. Bioeng., 85(6):589-600).*
Mercille et al (1999, Biotechnol. Bioeng., 63(5):529-43).*
Verma et al. (Nature 1997, 389:239-242).*
Amalfitano et al. (Current Gene Therapy 2002, 2: 111-133).*
Pandha et al. (Current Opinion in Investigational Drugs 2000; 1 (1): 122-134).*
Mader, et al., "A steroid-inducible promoter for the controlled overexpression of cloned genes in eukaryotic cells", *Proc. Natl. Acad. Sci. USA*, 90:5603-5607 (1993).
Elliott, et al., "Bcl-2 inhibits early apoptotic events and reveals post-mitotic multinucleation without affecting cell cycle arrest in human apithelial tumor cells exposed to etoposide", *Cancer Chemotherapy Pharmacology*, 44:1-11 (1999).
Mastrangelo, Alison J., et al. "Part I. Bcl-2 and Bcl-$x_L$ Limit Apoptosis upon Infection with Alphavirus Vectors", *Biotechnology and Bioengineering* (2000) 67(5):544-554.

(Continued)

*Primary Examiner*—Sean E Aeder
(74) *Attorney, Agent, or Firm*—DLA Piper LLP (US)

(57) ABSTRACT

The present invention relates to preventing or delaying programmed cell death by expressing one or more anti-apoptotic polypeptides in a cell such that programmed cell death in the cell is prevented or delayed. The present invention also relates to increasing production of a cell-related product by expressing one or more anti-apoptotic polypeptides in a cell such that production of the cell-related product by the cell is increased. Recombinant cells useful for producing cell-related product or cellular therapy are also provided.

46 Claims, 34 Drawing Sheets

OTHER PUBLICATIONS

Mastrangelo, Alison J., et al. "Part II. Overexpression of *bcl-2* Family Members Enhances Survival of Mammalian Cells in Response to Various Culture Insults", *Biotechnology and Bioengineering* (2000) 67(5):555-564.

Figueroa, Jr., Bruno, et al. "Comparison of Bcl-2 to a Bcl-2 Deletion Mutant for Mammalian Cells Exposed to Culture Insults", *Biotechnology and Bioengineering* (2001) 73(3):211-222.

Figueroa, Jr., Bruno, et al. "Aven and Bcl-$x_L$ Enhance Protection Against Apoptosis for Mammalian Cells Exposed to Various Culture Conditions", *Biotechnology and Bioengineering* (2001) 85(6):589-600.

Montal, M. "Mitochondria, glutamate nuerotoxicity and the death cascade", *Biochimica et Biophysica Acta* (1998) 1366:113-126.

Ricci, J.E., et al. "Récepteurs de surface et signaux intracellulaires impliqués dans la régulation de l'apoptose", *Immuno Analyse et Biologie Specialise*, ed. Scientitiques Elsevier, Paris, FR (1998) 13(6):339-349.

Charbonneau, Joel, et al. "Protection of hybrdoma cells against apoptosis by a loop domain-deficient Bcl-xL protein", *Cytotechnology* (2001) 37:41-47.

Chiang, Gisela G., et al. "Bcl-$x_L$ Mediates Increased Production of Humanized Monoclonal Antibodies in Chiense Hamster Ovary Cells", *Biotechnology and Bioengineering* (2005) 91(7):779-792.

Figueroa, Jr., Bruno, et al. "A comparison of the properties of a Bcl-$X_L$ variant to the wild-type anti-apoptosis inhibitor in mammalian cell cultures", *Metabolic Engineering* (2003) 5:230-245.

Fussenegger, Martin, et al. "Controlled profileration by multigene metabolic engineering ehances the productivity of Chinese hamster ovary cells", *Nature Biotechnology* (1998) 16(5):468-472.

González-Garcia, Maribel, et al. "*bcl-$X_L$* is the major *bcl-x* mRNA form expressed during murine development and its product localizes to mitochondria", *Development* (1994) 120:3033-3042.

Goswami, J., et al. "Apoptosis in Batch Cultures of Chinese Hamster Ovary Cells", *Biotechnology and Bioengineering* (1999) 62(6) 632-640.

Inohara, Naohiro, et al. "Mtd, a Novel Bcl-2 Family Member Activates Apoptosis in the Absence of Heterodimerization with Bcl-2 and Bcl-$X_L$", *The Journal of Biological Chemistry* (1998) 273(15):8705-8710.

Kim, No Soo, et al. "Overexpression of *bcl-2* Inhibits Sodium Butyrate-Induced Apoptosis in Chinese Hamster Ovary Cells Resulting in Enhanced Humanized Antibody Production", *Biotechnology and Bioengineering* (2000/2001) 71(3):184-193.

Mastrangleo, Alison J., et al. "Part I. Bcl-2 and Bcl-$x_L$ Limit Apoptosis upon Infection with Alphavirus Vectors", *Biotechnology and Bioengineering* (2000) 67(5):544-554.

Mastrangelo, Alison J., et al. "Part II. Overexpression of *bcl-2* Family members Enhances Survival of Mammalian Cells in Response to Various Culture Insults", *Biotechnology and Bioengineering* (2000) 67(5):555-564.

Meents, Heiko, et al. "Impact of Coexpression and Coamplification of sICAM and Antiapoptosis Determinants *bcl-2/bcl-$x_L$* on Productivity, Cell Survival, and Mitochondria Number in CHO-DG44 Grown in Suspension and Serum-Free Media", *Biotechnology and Bioengineering* (2002) 80(6):706-716.

Zanghi, James A., et al. "Serum Protects Protein-Free Competent Chinese Hamster Ovary Cells Against Apoptosis Induced by Nutrient Deprivation in Batch Culture", *Biotechnology and Bioengineering* (1999) 64(1):108-119.

\* cited by examiner

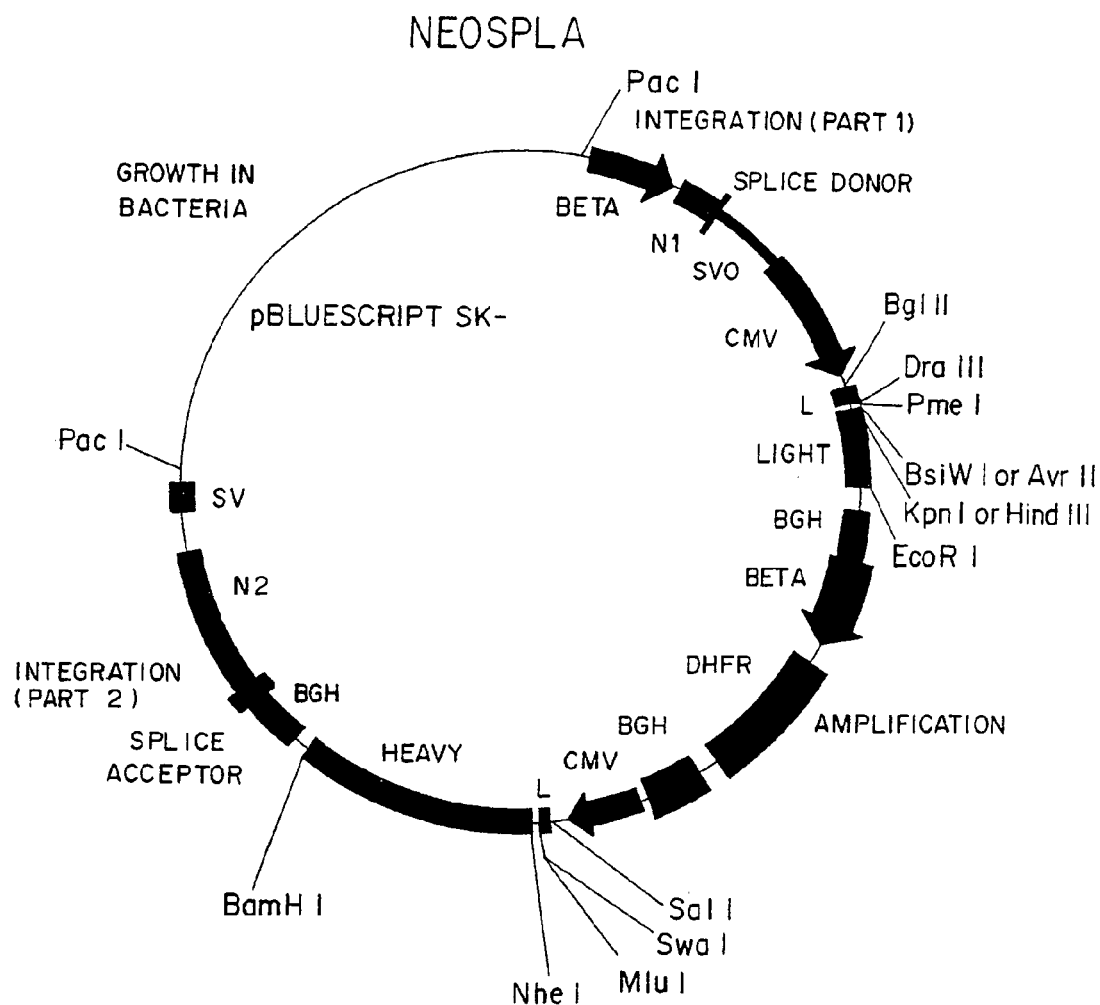

FIG. 1

CMV = Cytomegalovirus promoter/enhancer
BETA = Mouse Beta globin major promoter
SVO = SV40 origin
BGH = Bovine growth hormone polyadenylation
SV = SV40 polyadenylation
N1 = Neomycin phosphotransferase exon 1
N2 = Neomycin phosphotransferase exon 2
LIGHT = Human immunonoglobulin kappa or lambda constant region
DHFR = Dihydrofolate Reductase
HEAVY = Human immunonoglobulin gamma 1 or gamma 4 PE constant region
L = Leader

FIG. 2

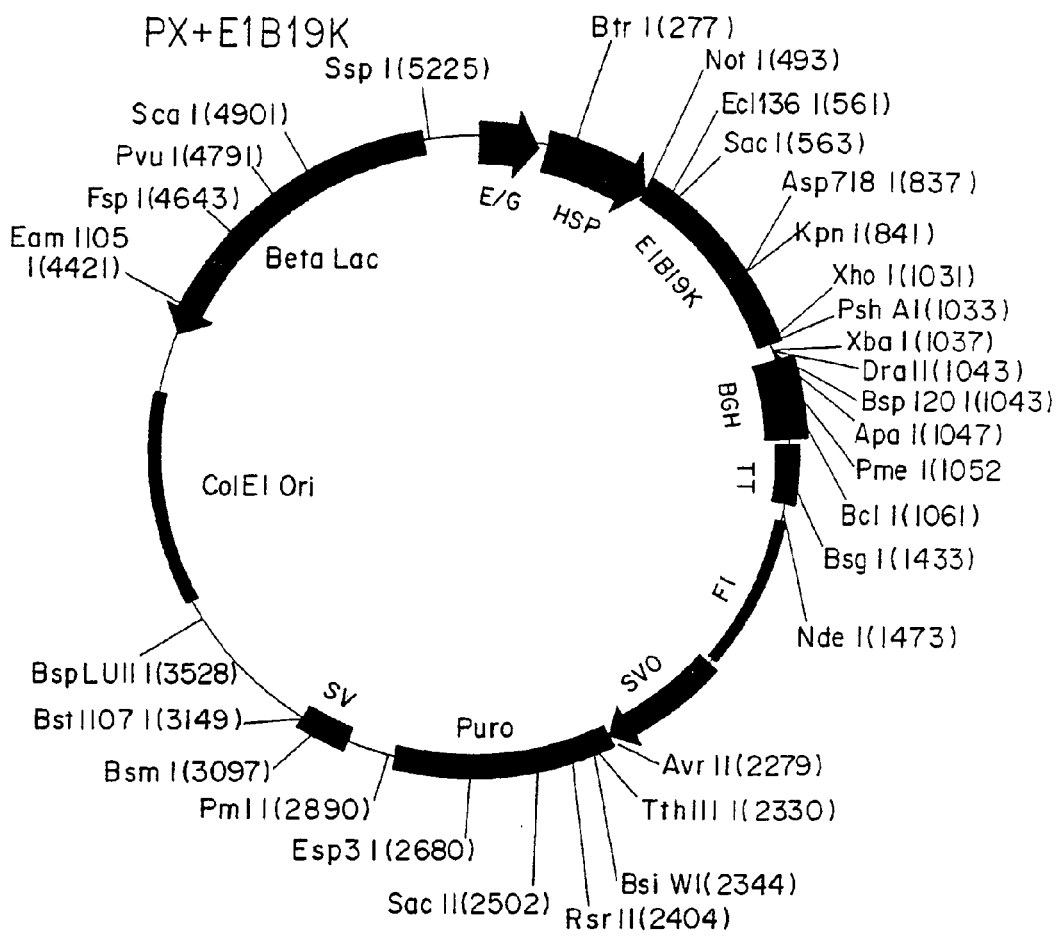

E/G + 5 x Ecdysone/Glucocorticoid Response Elements
E1B19K = Anti Apoptotic Gene (JHU)
TT = Transcription Terminator
SVO = SV40 early promoter/enhancer & origin
SV = SV40 early polyadenylation HSP = Minimal Heat Shock Promoter
BGH = Bovine growth hormone polyadenylation
F1 = F1 origin
Puro = Puromycin resistance gene The following restriction enzymes do not cut: AflII, AgeI, AscI, BaeI, BamHI, BbvCI, BglII, BspEI, BsrGI, BstBI, BstXI, Bsu36I, ClaI, Eco47III, EcoNI, EcoRI, EcoRV, FseI, HindIII, HpaI, I-PpoI, I-SceI, MamI, MluI, MunI, NheI, NruI, PacI, PflMI, PpuMI, SanDI, SbfI, SfiI, SgfI, SgrAI, SnaBI, SpeI, SrfI, SwaI, XcmI Constructed by Tri Huynh        10/16/2000 5343 bp

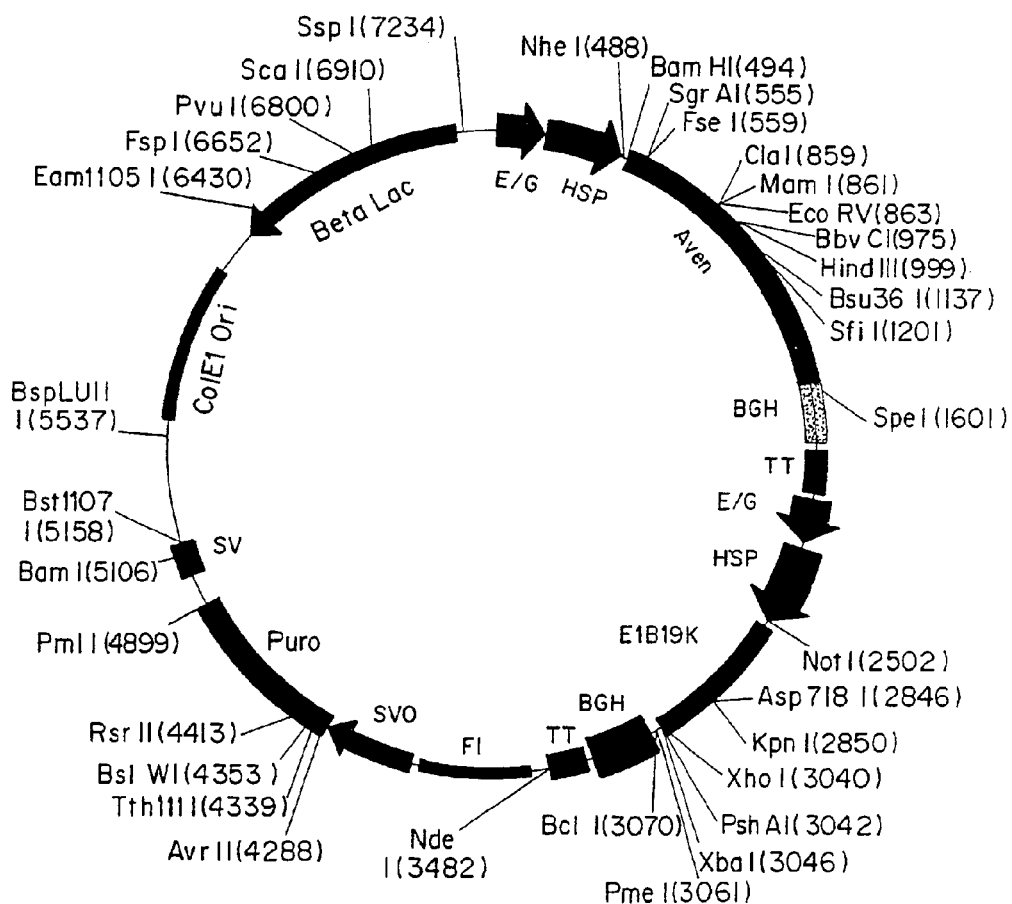

FIG. 3

PX + Aven + E1B19K

E/G = 5 x Ecdysone/Glucocorticoid Response Elements
Aven = Anti Apoptotic Gene (JHU)
TT = Transcription Terminator
F1 = F1 origin
Puro = Puromycin resistance gene HSP = Minimal Heat Shock Promoter
BGH = Bovine growth hormone polyadenylation
E1B19K = Anti Apoptotic Gene (JHU)
SVO = SV40 early promoter/enhancer & origin
SV = SV40 early polyadenylation The following restriction enzymes do not cut: AflII, AgeI, AscI, BaeI, BspEI, BsrGI, BstBI, BstXI, Eco47III, EcoNI, HpaI, I-PpoI, I-SceI, MluI, MunI, NruI, PacI, PflMI, SanDI, SbfI, SgfI, SnaBI, SrfI, SwaI, Xcm I Constructed by Tri Huynh    10/18/2000  7352 bp

Aven cDNA polynucleotide and Aven polypeptide amino acid sequences

The IDEC Aven polynucleotide sequence has a mutation in the second codon (improved Kozak) as compared to the published native Aven sequence whereby the native CAG has changed to AAC (underlined) in the IDEC sequence. This codon change results in a change from glutamine (Q) as the second amino acid residue of the published native polypeptide to asparagine (N, underlined) ion the IDEC Aven polypeptide.

IDEC'S Aven cDNA sequence:

ATGAACGCGGAGCGAGGAGCTCGGGGAGGCCGTGGGCGGCGGCCAGGCCGC
GGCCGGCCTGGCGGAGATCGCCACAGCGAGCGGCCCGGAGCCGCAGCGGCG
GTAGCCAGAGGCGGCGGCGGAGGCGGCGGCGGGGACGGAGGCGGACGCCG
GGGCCGTGGCCGTGGCCGGGGCTTCCGCGGCGCTCGCGGAGGCCGAGGAGG
AGGAGGCGCCCCGCGAGGCAGCCGCCGGGAGCCGGGAGGCTGGGGCGCAGG
GGCCAGCGCGCCGGTTGAAGATGACAGCGATGCAGAGACCTATGGAGAAGA
GAATGATGAACAGGGAAATTATTCTAAAAGAAAGATTGTCTCTAACTGGGAT
CGATATCAAGATATTGAAAAGAGGTCAATAATGAAAGTGGAGAGTCACAG
AGGGGAACAGATTTCAGTGTCCTCCTTAGCTCTGCAGGGGACTCATTCTCACA
GTTCCGGTTTGCTGAGGAGAAAGAATGGGATAGTGAAGCTTCTTGTCCAAAA
CAGAATTCAGCATTTTATGTGGATAGTGAGTTATTGGTTCGAGCCCTTCAAGA
GCTGCCTCTCTGCCTCCGACTCAACGTTGCTGCCGAACTGGTCCAGGGTACAG
TTCCTTTAGAGGTTCCTCAGGTGAAACCAAAGAGAACTGATGATGGCAAGGG
ATTAGGGATGCAGTTAAAGGGGCCCTTGGGGCCTGGAGGAAGGGGGCCCATC
TTTGAGCTGAAATCTGTGGCTGCTGGCTGCCCTGTGTTGCTGGGCAAAGACAA
CCCAAGCCCGGGTCCTTCAAGGGATTCTCAGAAACCCACTTCCCCACTGCAG
TCAGCAGGAGACCATTTGGAAGAAGAACTAGATCTGTTGCTTAATTTAGATG
CACCTATAAAAGAGGGAGATAACATCTTACCAGATCAGACGTCTCAGGACCT
GAAATCCAAGGAAGATGGGGAGGTGGTCCAAGAGGAAGAAGTTTGTGCAAA
ACCATCTGTGACTGAAGAAAAAAACATGGAACCTGAGCAACCAAGTACCTCC
AAAAATGTTACCGAGGAAGAGCTGGAAGACTGGTTGGACAGCATGATTTCCT
AA

IDEC's Aven polypeptide sequence

MNAERGARGGRGRRPGRGRPGGDRHSERPGAAAAVARGGGGGGGDGGGRR
GRGRGRGFRGARGGRGGGGAPRGSRREPGGWGAGASAPVEDDSDAETYGEEN
DEQGNYSKRKIVSNWDRYQDIEKEVNNESGESQRGTDFSVLLSSAGDSFSQFRFA
EEKEWDSEASCPKQNSAFYVDSELLVRALQELPLCLRLNVAAELVQGTVPLEVP
QVKPKRTDDGKGLGMQLKGPLGPGGRGPIFELKSVAAGCPVLLGKDNPSPGPSR
DSQKPTSPLQSAGDHLEEELDLLLNLDAPIKEGDNILPDQTSQDLKSKEDGEVVQ
EEEVCAKPSVTEEKNMEPEQPSTSKNVTEEELEDWLDSMIS

FIG. 4

E1B-19K cDNA polynucleotide and E1B-19K polypeptide amino acid sequences

Adenovirus E1B-19K Types 5 and 2, and their respective translated polypeptide sequences are shown below The construct used by IDEC is of Type 5. Type 2 is shown for the sake of comparison. The disparate regions between the adenovirus type 2 and type 5 translated polypeptide sequence, set out below, are underlined in the sequence listing.

Type 2 – Q   EEARR
Type 5 – QQQEEA  R

E1B-19K (adenovirus type 5) published cDNA sequence:

ATGGAGGCTTGGGAGTGTTTGGAAGATTTTTCTGCTGTGCGTAACTTGCTGGAACAGAGCTCTAACAG
TACCTCTTGGTTTTGGAGGTTTCTGTGGGGCTCATCCCAGGCAAAGTTAGTCTGCAGAATTAAGGAGG
ATTACAAGTGGGAATTTGAAGAGCTTTTGAAATCCTGTGGTGAGCTGTTTGATTCTTTGAATCTGGGTC
ACCAGGCGCTTTTCCAAGAGAAGGTCATCAAGACTTTGGATTTTTCCACACCGGGGCGCGCTGCGGCT
GCTGTTGCTTTTTTGAGTTTTATAAAGGATAAATGGAGCGAAGAAACCCATCTGAGCGGGGGGTACCT
GCTGGATTTTCTGGCCATGCATCTGTGGAGAGCGGTTGTGAGACACAAGAATCGCCTGCTACTGTTGTC
TTCCGTCCGCCCGGCGATAATACCGACGGAGGAGCAGCAGCAGCAGCAGGAGGAAGCCAGGCGGCGG
CGGCAGGAGCAGAGCCCATGGAACCCGAGAGCCGGCCTGGACCCTCGGGAATGA

E1B-19K (adenovirus type 5) published polypeptide sequence:

MEAWECLEDFSAVRNLLEQSSNSTSWFWRFLWGSSQAKLVCRIKEDYKWEFEELLKSCGELFDSLNLGHQ
ALFQEKVIKTLDFSTPGRAAAAVAFLSFIKDKWSEETHLSGGYLLDFLAMHLWRAVVRHKNRLLLLSSVRP
AIIPTEEQQQQQEEARRRRQEQSPWNPRAGLDPRE

E1B-19K (adenovirus type 2) published cDNA sequence:

ATGGAGGCTTGGGAGTGTTTGGAAGATTTTTCTGCTGTGCGTAACTTGCTGGAACAGAGCTCTAACAG
TACCTCTTGGTTTTGGAGGTTTCTGTGGGGCTCATCCCAGGCAAAGTTAGTCTGCAGAATTAAGGAGG
ATTACAAGTGGGAATTTGAAGAGCTTTTGAAATCCTGTGGTGAGCTGTTTGATTCTTTGAATCTGGGTC
ACCAGGCGCTTTTCCAAGAGAAGGTCATCAAGACTTTGGATTTTTCCACACCGGGGCGCGCTGCGGCT
GCTGTTGCTTTTTTGAGTTTTATAAAGGATAAATGGAGTGAAGAAACCCATCTGAGCGGGGGGTACCT
GCTGGATTTTCTGGCCATGCATCTGTGGAGAGCGGTGGTGAGACACAAGAATCGCCTGCTACTGTTGT
CTTCCGTCCGCCCGGCAATAATACCGACGGAGGAGCAACAGCAGGAGGAAGCCAGGCGGCGGCGGCG
GCAGGAGCAGAGCCCATGGAACCCGAGAGCCGGCCTGGACCCTCGGGAATGA

E1B-19K (adenovirus type 2) published polypeptide sequence:

MEAWECLEDFSAVRNLLEQSSNSTSWFWRFLWGSSQAKLVCRIKEDYKWEFEELLKSCGELFDSLNLGHQ
ALFQEKVIKTLDFSTPGRAAAAVAFLSFIKDKWSEETHLSGGYLLDFLAMHLWRAVVRHKNRLLLLSSVRP
AIIPTEEQQQEEARRRRRQEQSPWNPRAGLDPRE

FIG. 5

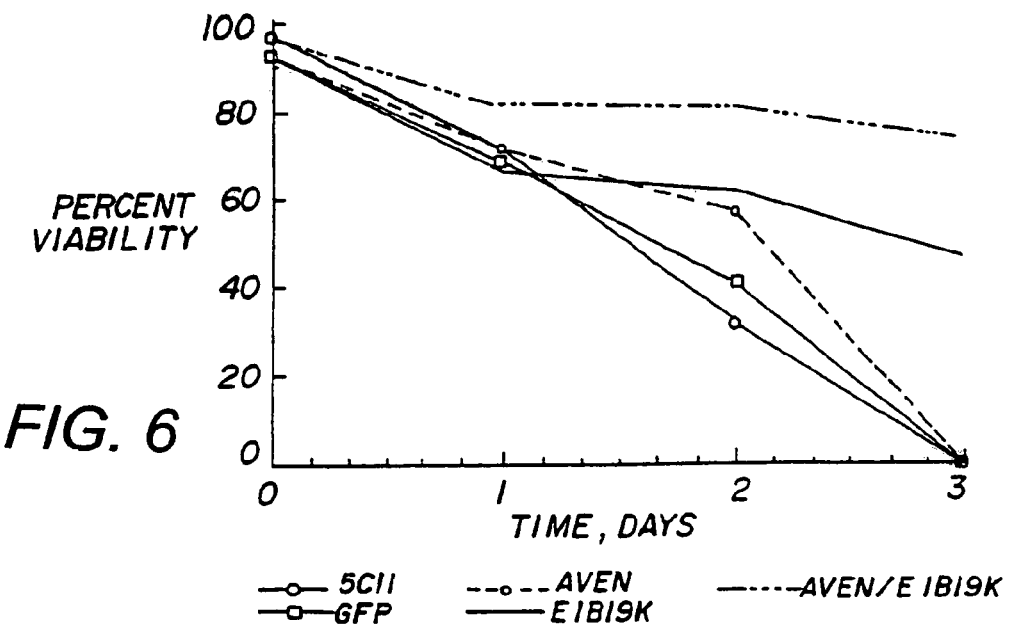
FIG. 6  6-WELL GLUCOSE DEPRIVATION EXPERIMENTS. CELL POPULATIONS WERE INDUCED WITH 5 mcM Ponasterone A FOR 48 HOURS BEFORE START OF EXPERIMENT
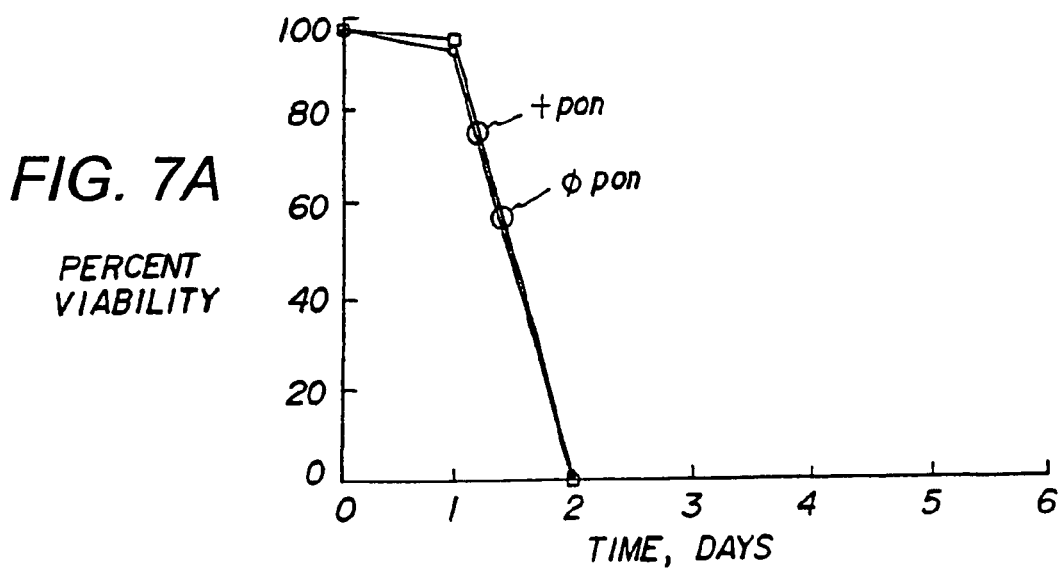
FIG. 7A  GFP STABLE CELL POOLS

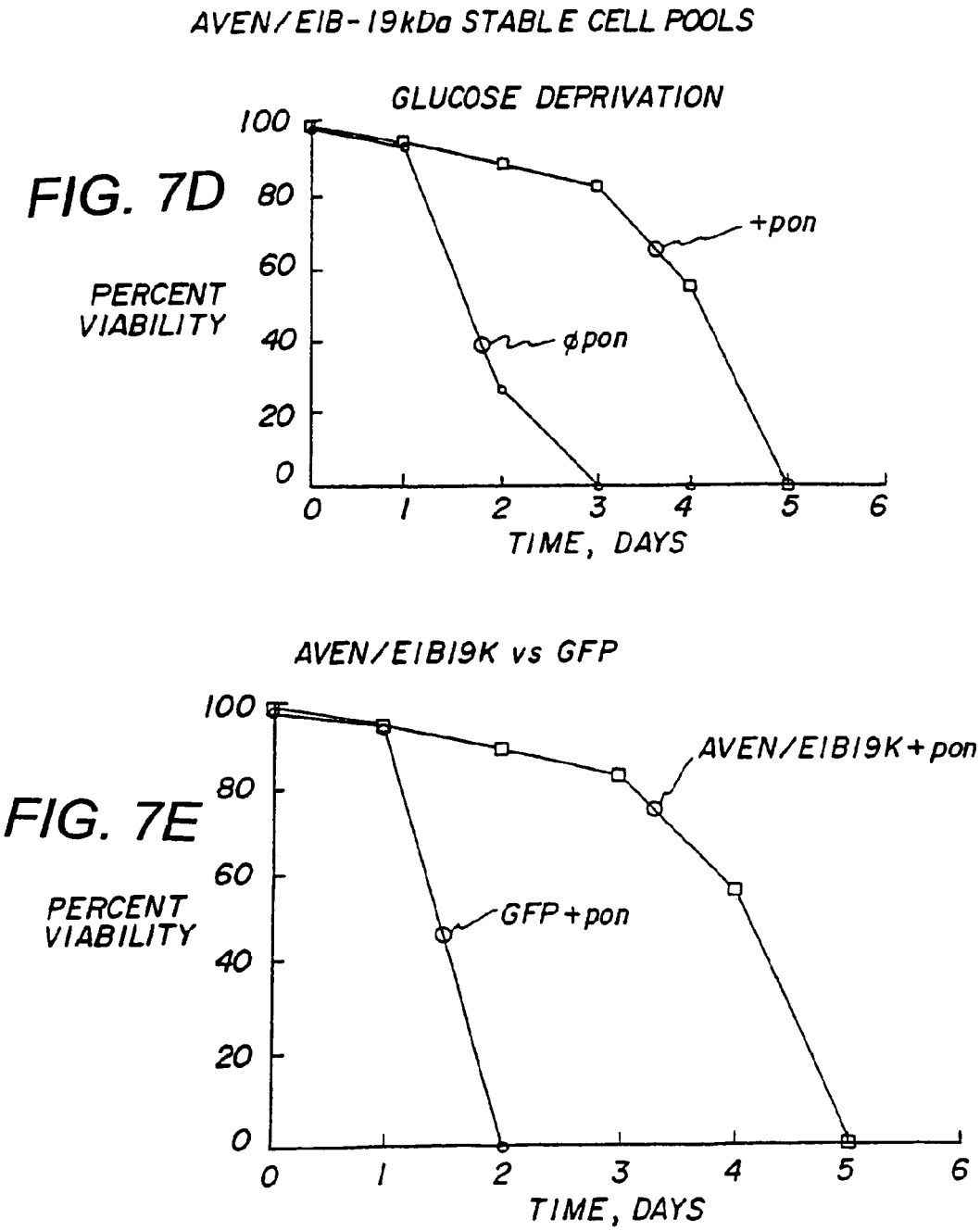

Apoptosis Induced by Various Culture Conditions. DNA analysis of CHO cells: (A) following exposure to staurosporine (B) post-seru-withdrawal (C) post-SV infection (D) following exposure to 5-day spent medium and (E) following exposure to 4-day spent medium.

INDUCIBLE EXPRESSION OF ANTI-APOPTOSIS GENES
Populations were induced
Using 5μM ponasterone A
α-GFP
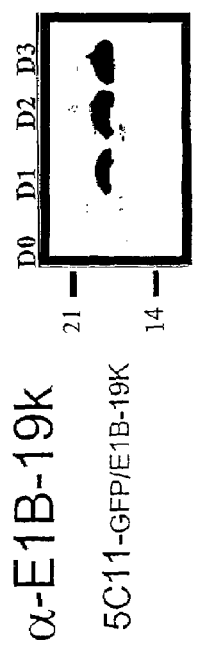
α-AVEN
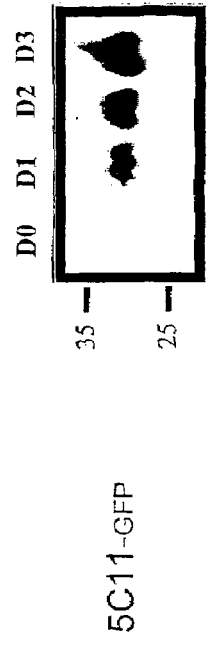
α-E1B-19k
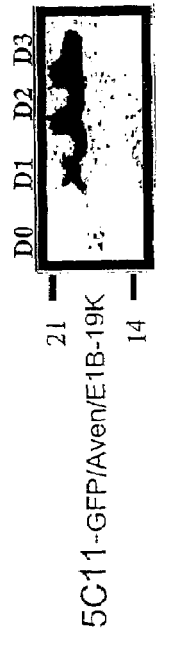
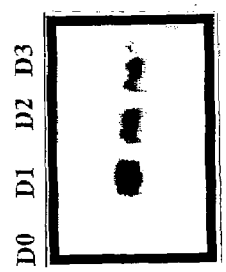
FIG. 14

GLUCOSE DEPRIVATION STUDIES

6-WELL GLUCOSE DEPRIVATION EXPERIMENTS. CELL POPULATIONS WERE INDUCED WITH 5 mcMPonasterone A FOR 48 HOURS BEFORE START OF EXPERIMENT

SPINNER FLASK STUDIES

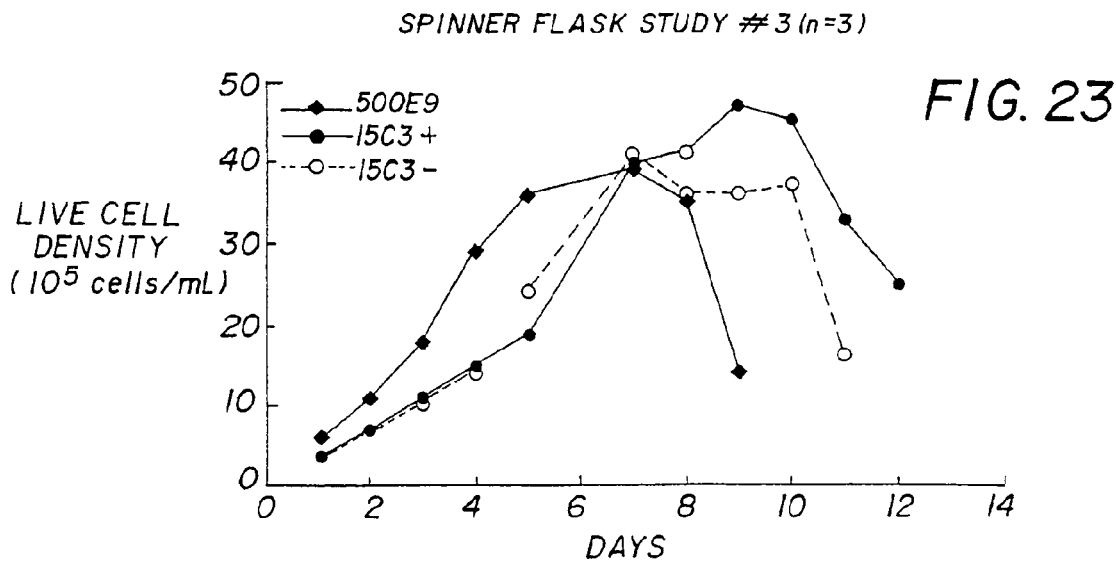
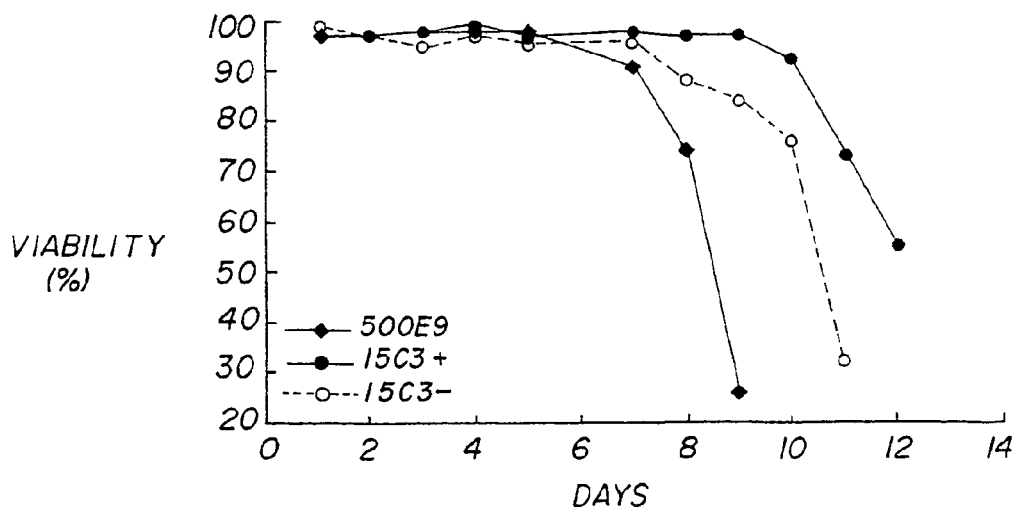

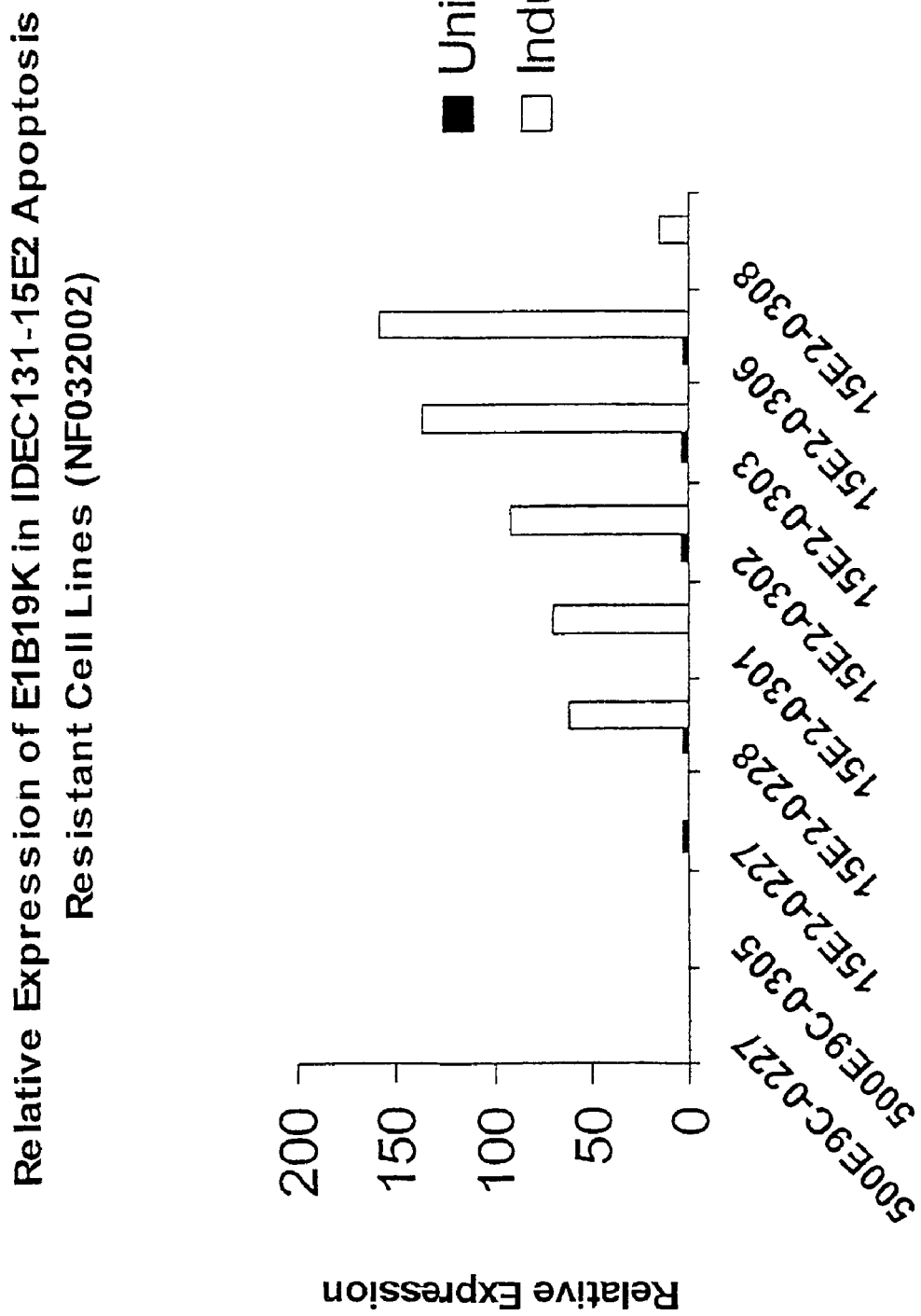

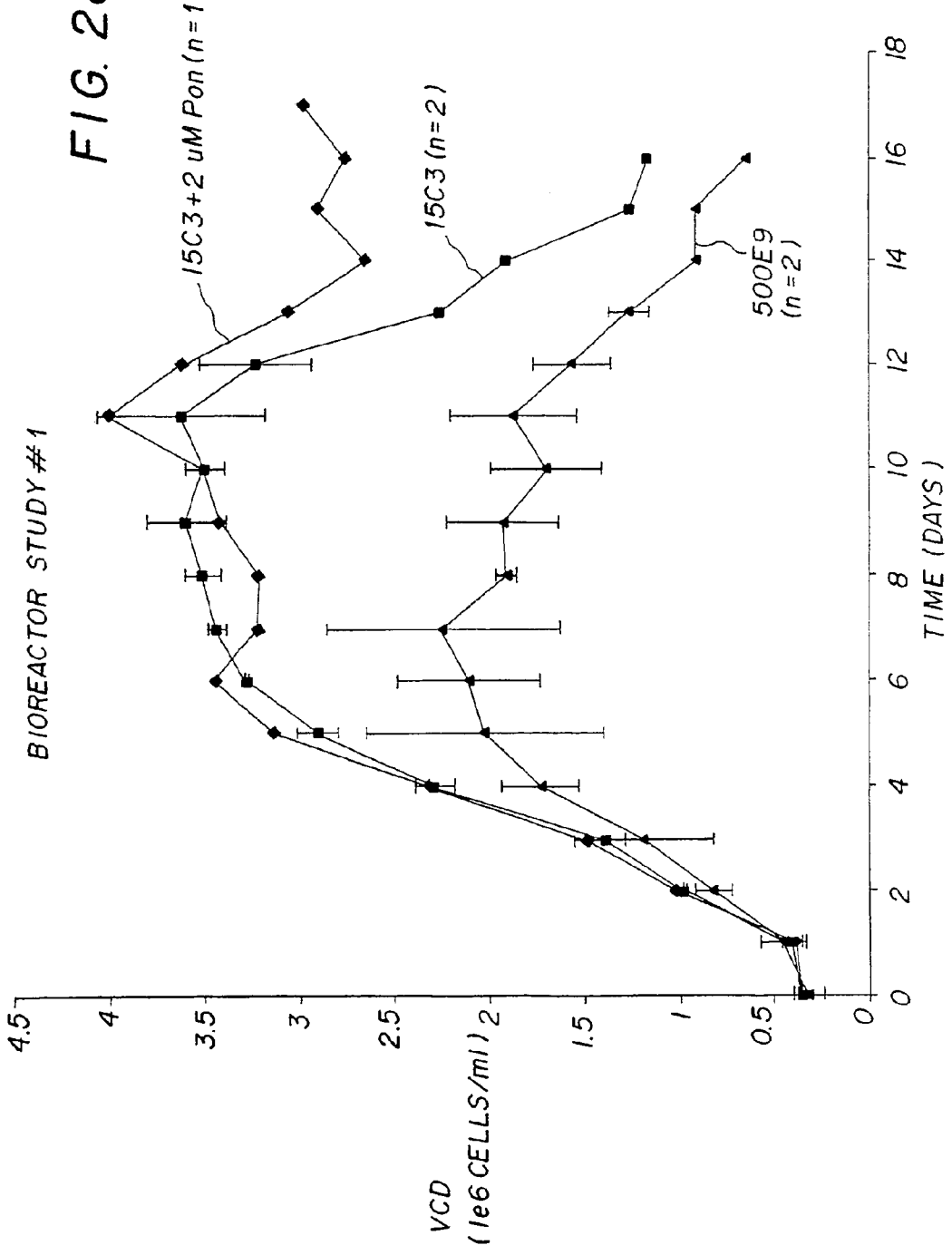

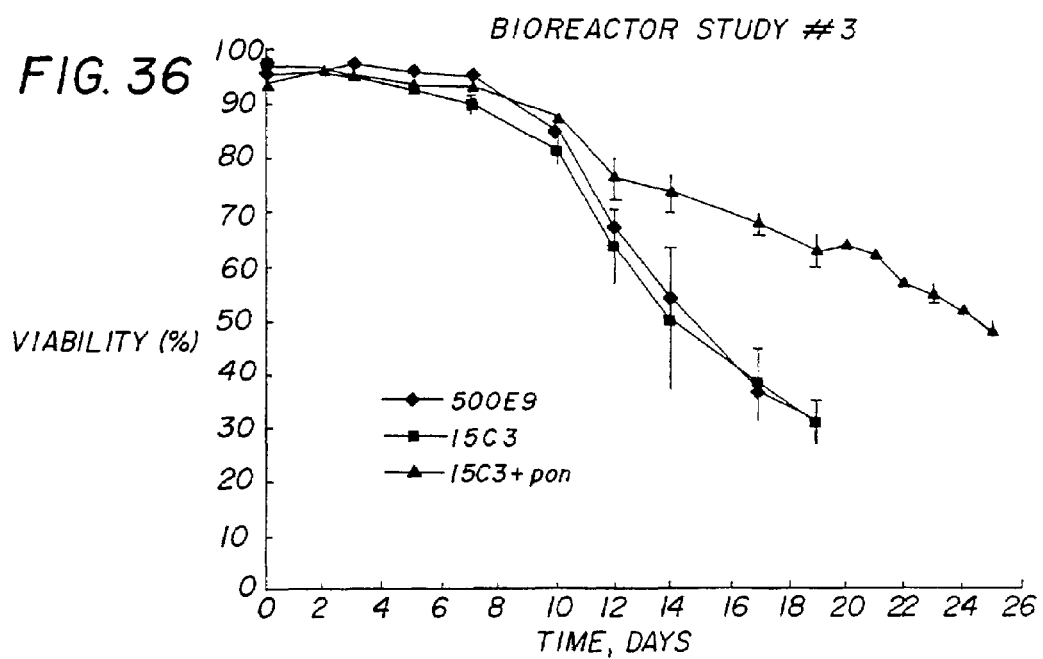
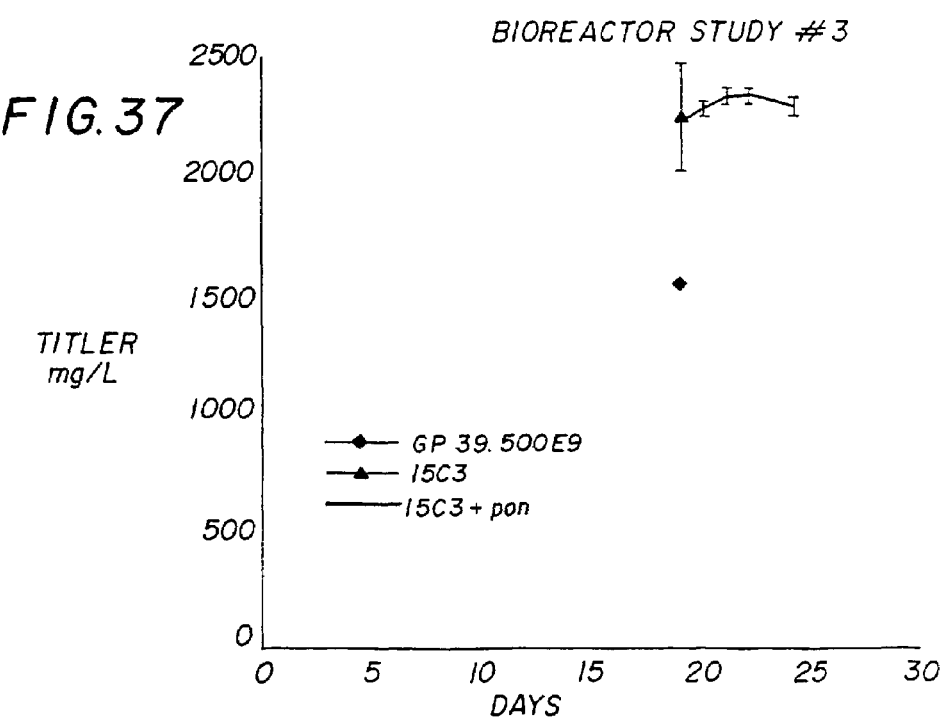

INHIBITION OF APOPTOSIS PROCESS AND IMPROVEMENT OF CELL PERFORMANCE

RELATED APPLICATIONS

This application claims priority to U.S. provisional application 60/303,813 filed Jul. 10, 2001 incorporated by reference in its entirety.

FIELD OF THE INVENTION

The present invention relates to preventing or delaying programmed cell death in a recombinant cell. More specifically, the present invention relates to inhibiting programmed cell death in a recombinant cell by expressing one or more anti-apoptotic polypeptides in the cell.

The present invention further relates to increasing a recombinant cell's production of a cell-related product, e.g., recombinant protein such as an antibody by expressing one or more anti-apoptotic polypeptides in the cell. In addition, the present invention provides recombinant cells expressing anti-apoptotic polypeptides. Such cells are useful for cellular therapy or for producing cell-related products, especially in large-scale bioreactors of commercial production.

BACKGROUND OF THE INVENTION

The production of high value therapeutic or diagnostic proteins by eukaryotic cells in the pharmaceutical or commercial manufacturing environment is subject to stringent constraints with regard to available fermentation vessel volume and fermentation process time. From the perspective of a manufacturing fermentation suite over a period of time, production efficiency comes from maximizing the rate of protein production per unit time while in operation, and minimizing the operational down time, and minimizing the fraction of operating time during which the production rate is low.

One broad approach to increasing protein productivity in the manufacturing setting is to increase the density of the cells in the vessel. Considerable increases in cell density can be achieved through the development of appropriately balanced culture medium formulations, by nutrient feeding approaches, and by perfusion of medium through systems that retain the cells. These approaches, in addition to increasing cell density, can also be effective in increasing the overall lifetime of batch cultures.

Another basic approach to increasing manufacturing productivity is to increase the rate of protein production by the cells, themselves, i.e., increasing the specific cellular productivity (amount of protein produced/cell/day). Traditionally, the way in which cells with high rates of productivity are attained comes about as a multi-step process in which, first, a large population of cells are transected with the gene for the protein of interest, and second, single cell clones of the larger population are grown out, and the higher producing cell lines are identified and selected for further cell line development. The heterogeneity with regard to protein production rate that manifests in a transfected cell population is generally ascribed to differences primarily in the position of integration of the new genetic material into the host cell's genome and secondarily in the total number of DNA sequences integrated (the copy number). Accordingly, methods for targeting the site of heterologous DNA integration into the host genome have also been developed, such that the DNA sequences can be integrated into sites associated with high levels of transcription into RNA. Examples of these approaches are provided by U.S. Pat. Nos. 5,648,267, 5,733,779, 6,017,733 and 6,159,730 pertaining to the NEOSPLA vector, and U.S. Pat. Nos. 5,830,698 and 5,998,144 pertaining to homologous recombination.

Also, co-transfection of the gene for the protein of interest with another gene for a protein that confers resistance to toxic agent offers a way to select for high producing cells. By exposing growing cells to increasing concentrations of such a toxic agent, cells with higher copy number of the resistance gene are selected. These cells are often found to have undergone a process of genomic amplification of the resistance gene. Co-amplification of the adjacent gene coding for the protein of interest often leads to an increase in the level of cellular specific production of the desired protein (Ringold, J. Mol. Appl. Genetic 1(3): 165-75 (1981); Kaufman, J. Mol. Biol. 159(4): 601-21 1982).

In an area of biological research with an origin entirely separate from the biochemical engineering of cell culture manufacturing processes, a great deal has been learned over the past decade about apoptosis, a process of programmed cell death. The conceptual breakthrough accompanying these developments is that there is a natural physiological process, which results in cell death. Cell death, of course, can also occur as a direct and immediate result of trauma, which destroys cell integrity, whereupon the cell or its remnants proceed to necrosis. Apoptosis can be initiated by a wide variety of circumstances or stimuli, natural or developmental in nature, as part of a disease process, or in response to physiological stress. Developmental processes, whereby organs mature or reorganize, for example, can involve the death of specific kinds of cells, to make way for the emergence of other new kinds of cells. Understanding apoptosis at the genetic and biochemical levels, and the search for ways in which to intervene, either to promote it or to stop it, has thus emerged as an area of considerable interest in medical sciences.

Apoptosis, however, has also become appreciated as a major route for the cell death that occurs as a matter of course during in vitro culture of mammalian cells. A basic form of cell culture, done both in the laboratory and in large scale manufacturing environments, is termed batch culture. A batch culture is initiated with a healthy, actively growing cell inoculant; the culture grows to a peak cell density, enters a period of decline, and runs a course until the cell population dies off. The latter declining phase of cell culture is a time when the environment becomes stressful to the cells, as nutrients become depleted, and the concentrations of toxic metabolites increases. Additionally, the fermentation environment, itself, can offer other stressful factors, such as shear forces created by the hardware, fluid and gas turbulence associated with mixing, and the movement of the culture through pipes and lines. All of these factors (nutrient limitation, toxic agents in the medium, and physical stresses) have been demonstrated to initiate apoptosis in cells in culture, and thus to play a role in the limiting the life expectancy of the culture as a whole.

Several of proteins that play key roles in the apoptotic process have recently been discovered, and their genes isolated and cloned. E1B-19K is an adenovirus protein, which is an anti-apoptotic member of the Bcl-2 protein family. The cell's response to an infection is to initiate the apoptosis cascade. This defense mechanism is used to eliminate infected cells from tissues. However, certain viruses have developed a method to combat the apoptosis response by encoding proteins expressed early in the infection process that suppress apoptosis. During adenoviral infection, the viral gene expression in cells is regulated by the E1 region of the adenovirus genome. The E1 region is composed of two transcription units, E1A and E1B. The E1B unit encodes two distinct tumor antigens of adenovirus, 19 kDa and 55 kDa proteins. An inhibitor of apoptosis, E1B-19K's action is understood to be similar to that of anti-apoptotic protein Bcl-2, which inhibits apoptosis at multiple stages in the cell death pathway. One mechanism of apoptotic suppression is thought to be through stabilization of the mitochondrial membrane, thereby preventing release of cytochrome C and other pro-apoptotic factors in the cytosol. (Vander Heiden Cell 91 (5): 627-37 (1997)). Cytochrome C is involved in binding to Apaf-1 in a complex involved in the initiation of the caspase cascade. Zou J. Biol. Chem. 274 (17): 11549-56 (1999). Bcl-2 family members (Bcl-$X_L$) also block activation of Apaf-1 by directly binding to Apaf-1. (Hu et al., J. Biol. Chem 273 (10): 5481-5 (1998); PNAS 95 (8): 4386-91 (1998)).

Another anti-apoptotic protein is Aven, a ubiquitous membrane protein. Aven's anti-apoptotic activity is attributed to its ability to inhibit caspase 9 activation by interfering with the self-association of the caspase activator Apaf-1 (Chau Mol. Cell. 6:31-40 (2000)). Aven has also been shown to enhance the anti-apoptotic activity of Bcl-$X_L$ in BHK (baby hamster kidney) cells, which suggests an interaction between Aven and Bcl-$X_L$ (Chau (2000)).

All of the above described various approaches to increasing protein productivity have succeeded in practice to varying degree. Nevertheless there is still a need to develop methods to increase production of cell-related product, e.g., recombinant proteins, especially in large-scale commercial production. In addition, there is a need to develop methods for prevention or delaying programmed cell death.

SUMMARY AND OBJECTS OF THE INVENTION

An object of the invention is to provide a method for preventing or delaying programmed cell death in a recombinant cell wherein the cell is not a mouse myeloma cell. The method includes expressing or inducing the expression of one or more anti-apoptotic polypeptides, e.g., cellular Bcl-$x_L$, Bcl-2, Aven, or viral proteins E1B-19K, and p35 in the cell such that programmed cell death in the cell is prevented or delayed, wherein when expressing one anti-apoptotic polypeptide in the cell the anti-apoptotic polypeptide is not a Bcl-$x_L$ interacting factor, e.g., Aven.

More specifically, it is an object of the present invention to provide a method for preventing or delaying programmed cell death in a recombinant cell containing one or more heterologous polynucleotides encoding one or more desired polypeptides, e.g., antibodies such as anti-CD154 (IDEC-131), anti-CD20 antibodies (e.g., RITUXAN®, a chimeric anti-CD20 having FDA approval for treatment of non-Hodgkin's lymphoma, which is produced by ATCC Accession No. 69119, Zevalin™), anti-CD80 (IDEC 114) antibodies, anti-CD23 antibodies (IDEC 152), anti-CD4 antibodies (IDEC 151), and anti-tumor antigen antibodies, enzymes, receptors, cytokines, cell-surface factors, cell metabolites, cell-secretion factors, viral factors, and membrane-associated factors.

It is another object of the invention to provide a method of increasing production of a cell-related product by a recombinant cell. The method includes expressing or inducing the expression of one or more anti-apoptotic polypeptides in the cell such that production of the cell-related product by the cell is increased, wherein when expressing one anti-apoptotic polypeptide in the cell the anti-apoptotic polypeptide is not a Bcl-$x_L$ interacting factor, e.g., Aven.

It is yet another object of the invention to provide a method of increasing production of a recombinant cell. The method includes expressing or inducing the expression of one or more anti-apoptotic polypeptides in the cell such that production of the recombinant cell is increased, wherein when expressing one anti-apoptotic polypeptide in the cell the anti-apoptotic polypeptide is not a Bcl-$x_L$ interacting factor, e.g., Aven.

It is another object of the invention to provide a recombinant cell useful for producing cell-related product. The recombinant cell expresses or can be induced to express at least two anti-apoptotic polypeptides.

It is yet another object of the invention to provide a population of cells useful for producing one or more biological functions of the cells. The population of cells express or can be induced to express at least two anti-apoptotic polypeptides.

It is still another object of the invention to provide a population of cells useful for cellular therapy. The population of cells express or can be induced to express one or more anti-apoptotic polypeptides.

BRIEF DESCRIPTION OF THE FIGURES

FIG. 1 depicts the NEOSPLA expression vector used to express the antibody IDEC 131.

FIG. 2 depicts the inducible expression vector, plasmid PX+E1B-19K.

FIG. 3 depicts the inducible expression vector, plasmid PX+Aven+E1B-19K.

FIG. 4 depicts the Aven cDNA polynucleotide and Aven polypeptide amino acid sequences (SEQ ID NOS 1-2, respectively).

FIG. 5 depicts the E1B-19K cDNA polynucleotide (SEQ ID NOS 3 and 5, respectively, in order of appearance) and E1B-19K polypeptide amino acid sequences (SEQ ID NOS 4 and 6, respectively, in order of appearance).

FIG. 6 depicts data with respect to cell viability: comparing the 3-day survival of glucose-deprived cultures of cells (1) transfected with GFP alone, (2) transfected with GFP+Aven, (3) transfected with GFP+E1B-19K, (4) transfected with GFP+Aven+E1B19K, and (5) non-transfected parental cells.

FIG. 7 depicts data with respect to cell viability: comparing the 3-day survival of glucose-deprived cultures of cells transfected (1) with GFP alone, (2) with GFP+Aven, (3) with GFP+E1B-19K, (4) with GFP+Aven+EIB19K, each culture in the presence and absence of steroid induction.

FIGS. 7A, 7B, 7C, 7D and 7E depicts data with respect to cell viability: comparing the 3-day survival of glucose-deprived cultures of cells transfected (1) with GFP alone, (2) with GFP+Aven, (3) GFP+Aven+B1B19K, each culture in the presence and absence of steroid induction.

FIG. 14 shows the inducible expression of anti-apoptosis genes α-Aven and α-E1B-19K in CHO cells.

FIGS. 23-26 contain other spinner flask results.

FIGS. 27A and 27B compare relative expression of IDEC 131 in different cell lines under induced or non-induced conditions.

FIGS. 28-31 contain the results of bioreactor study #1.
FIGS. 35-37 contain the results of bioreactor study #3.

DETAILED DESCRIPTION OF THE INVENTION

Figure 7B:
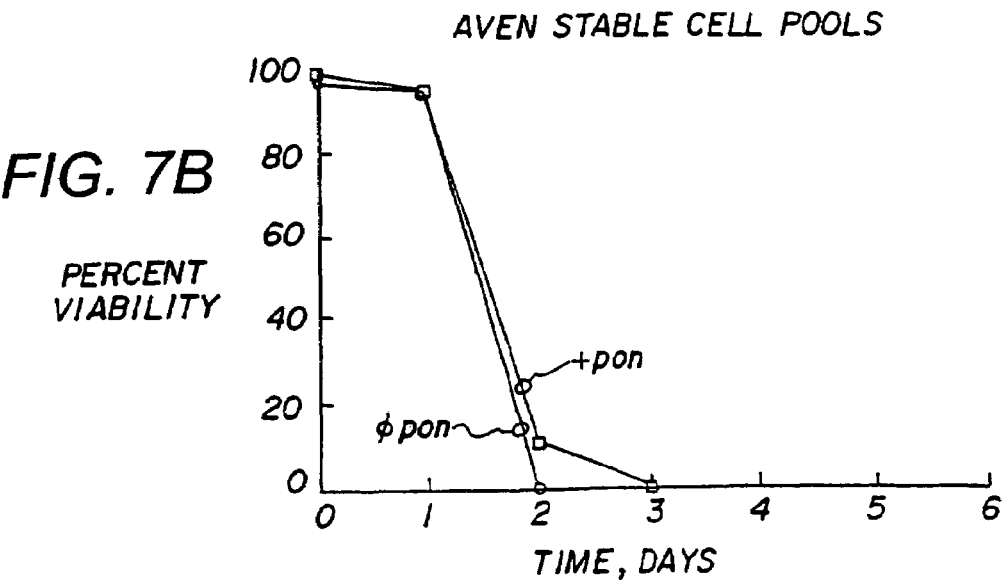

As described above, the present invention relates to prevention or delaying programmed cell death in a recombinant cell, especially a recombinant cell, preferably a mammalian cell producing cell-related product. It is a discovery of the present invention that inhibiting apoptosis in a cell increases cell viability and cell performance. Therefore the present invention provides methods to preventing or delaying programmed cell death in a recombinant cell by expressing one or more anti-apoptotic polypeptides in the cell. The present invention also provides methods to increasing production of a cell-related product in a recombinant cell by expression one or more anti-apoptotic polypeptides in the cell. In addition, the present invention provides recombinant cells useful for producing cell-related product or cellular therapy.

The capacity of this approach to inhibit cell death in mammalian and other eukaryotic cells in culture potentially can be used to improve production of any native or heterologous protein or virus produced by the cells of interest. Native and heterologous product targets of interest would include but are not limited to antibodies, cytokines, growth factors, hormones, serum proteins, receptors, enzymes, ligands, cell secretory factors, cell metabolites, and viral vectors that are produced by mammalian or other eukaryotic cells naturally or following genetic manipulation. The genetic manipulation techniques would include standard recombinant DNA techniques in which the target gene of interest is integrated into the mammalian genome or an extra-chromosomal element in order to allow expression of the integrated gene as a heterologous protein. The technology described in this application will be appropriate for all mammalian and other eukaryotic cell lines for which apoptosis occurs during the cell culture process. Appropriate cell lines include but are not limited to Chinese Hamster Ovary (CHO), Baby Hamster Kidney (BHK), human embryonic kidney (HEK) 293, NS0 myeloma, COS, NFO mammalian cells and other eukaryotic cells such Sf-9, Sf-21, and Trichoplusia ni insect cells. These cell lines can be obtained from sources such as American Type Culture Collection (ATCC). Such technology may be appropriate for any eukaryotic cells that undergo programmed cell death and can be genetically manipulated to generate heterologous proteins of interest such as those listed above.

Target proteins and viruses would include those that can be produced in a mammalian or other eukaryotic cells for biotechnology or pharmaceutical applications. Several possible proteins of interest for application with this technology include but are not limited to growth factors and cytokines such as human growth hormone, granulocyte-colony stimulating factor (growth factor), granulocyte macrophage colony stimulating factor, erythropoietin, interleukins 1 alpha and beta, 2, 3, 4, 6, 8, 10, 11, 13, 15, 17, and 18, interferon alpha and gamma, endothelial growth factor, epidermal growth factor, fibroblast growth factor, insulin, leptin, nerve growth factors, tumor necrosis factor-alpha, platelet derived growth factors, transforming growth factor, bone morphogenic protein, and stem cell factor; enzymes such as nucleases, trypsin, aprotinin, and kinases; cell culture reagents such as laminin, collagen, and fibronectin; plasma and serum proteins such as transferrin tissue plasminogen activator, plasminogen, plasmin, and thrombin and factors VIII, IX, and X; monoclonal antibodies to cytokines, cytokine receptors, growth factors, and other receptors, ligands, and cell-associated factors; receptors such as tumor necrosis factor receptors 1 and 2; erythropoietin receptors, transferrin receptors, interleukin receptors, leptin receptor, P and L selectins, ICAM, VCAM; ligands such as FAS ligand and CD ligands; metabolites such lipids, fats, nucleotides, and carbohydrates; viral vectors such as adenoviruses, retroviruses, and adeno-associated viruses. Although this list includes many currently produced heterologous protein and other product, the technology will be equally appropriate for other current and future proteins and products in which the producing eukaryotic cells in culture undergo apoptosis during the production process.

According to the present invention, expression of one or more anti-apoptotic polypeptides in a cell can be achieved by any suitable means known to one skilled in the art. For example, one can introduce one or more polynucleotide constructs encoding one or more anti-apoptotic polypeptides. Such constructs can be expression constructs and can include at least one inducible promoter operably linked to the polynucleotide encoding one or more anti-apoptotic polypeptides. In one embodiment, an ecdysone inducible system is used to control the expression of one or more anti-apoptotic polypeptides in a dose-dependent manner by a steroid. Such system is described in detail in U.S. Pat. No. 5,534,418, the entire contents of which is incorporated herein by reference.

Other promoters are also applicable. Examples of suitable viral transcription promoters useful in eukaryotic cells are those from simian virus 40, adenovirus, rous sarcoma virus and cytomegalovirus. Transacting transcription activators that stimulate transcription of heterologous genes can be employed to activate a promoter. For example, SV 40 T antigen, adenovirus E1A and E1B proteins can act on certain viral promoters of heterologous genes, including the CMV major intermediate early (MIE) promoter. Other molecules with transactivating activity include the immediate early proteins of herpes virus, C-myc, and genes of human and simian AIDS virus.

In another embodiment, the expression construct includes an inducible promoter and a screenable or selectable marker such that cells expressing one or more anti-apoptotic polypeptides can be selected or detected. Any suitable selection or screening markers can be used for the present invention, e.g., green fluorescence protein (GFP) or enhanced green fluorescence protein (EGF).

According to the present invention, one or more anti-apoptotic polypeptide can be expressed. Anti-apoptotic polypeptide includes any polypeptides having an activity of inhibiting or decreasing apoptosis in a cell. For example, an anti-apoptotic polypeptide can be encoded by heterologous polynucleotides, e.g., genes in eukaryotic cells or viruses. In one embodiment, an anti-apoptotic polypeptide is a member of Bcl-2 family, Aven family, adenovirus or baculovirus antideath protein family, or a fragment thereof. In another embodiment, an anti-apoptotic polypeptide is Bcl-2, Bcl-$x_L$, Aven, E1B-19K, or p35. In yet another embodiment, when expressing one anti-apoptotic polypeptide, it is not Aven, a Bcl-$x_L$ interacting factor, a factor protecting cells from caspase-1 induced apoptosis, a factor inhibiting the activation of caspases by cytochrome c and dATP, a factor that binds to anti-apoptosis Bcl-2 members, or a factor that binds to Apaf-1.

In a recombinant cell, anti-apoptotic polypeptide can be expressed alone or in combination with others. For example, one can express just Aven or co-express Aven and E1B-19K. One or more expression constructs can be used to express two or more anti-apoptotic polypeptides. In one embodiment, a recombinant cell expresses Aven in combination with one or more other anti-apoptotic polypeptides.

Recombinant cells of the present invention include any suitable cells known and available to one skilled in the art. In one embodiment, the recombinant cells are mammalian cells, e.g., human, murine, or rodent cells. In another embodiment, the recombinant cells are BHK cells or CHO cells such as CHO 5C11. In addition, methods of the present invention can be applied to recombinant cells in a large-scale bioreactor or culture device of commercial production. Other suitable cells include COS, CV-1, SP2/0 and hybridomas.

According to one embodiment, recombinant cells of the present invention contain one or more heterologous polynucleotides encoding one or more desired polypeptides. Such polypeptides can be any including without limitation antibodies, enzymes, receptors, cytokines, cell-surface factors, cell metabolites, cell-secretion factors, viral factors, and membrane-associated factors. In one embodiment, such polypeptides are antibodies including without limitation anti-CD154 (gp 39) antibodies (IDEC-131), anti-CD20 (Rituxan®, Zevalin™) antibodies, anti-CD80 (B7.1) antibodies (IDEC 114), anti-CD23 antibodies (IDEC 152), anti-CD4 antibodies (IDEC 151), and anti-tumor antigen antibodies.

According to another feature of the present invention, expressing one or more anti-apoptotic polypeptides increases production of a cell-related product by a recombinant cell. A cell-related product can be any product produced because of cell performance. For example, a cell-related product can be expression of recombinant or endogenous proteins, antibodies, enzymes, receptors, cytokines, cell-surface factors, membrane-associated factors, or polynucleotides. In one embodiment, a cell-related product is a viral factor, a cell metabolite, or any cellular components. In another embodiment, a cell-related product can be the cell itself.

The present invention also provides recombinant cells useful for producing cell-related product. These cells express or can be induced to express one or more anti-apoptotic polypeptides. In one embodiment, these cells express at least two anti-apoptotic polypeptides. These cells can also be used for cellular therapy because of their increased viability and cell performance, e.g., increased production of cell-related product.

To further illustrate the invention, the following examples are provided. These examples are not intended, nor are they to be construed, as further limiting the invention.

Example 1

Vectors and Transfection

An IDEC proprietary expression vector, referred to as NEOSPLA (FIG. 1), contains the neomycin phospotransferase gene divided into exons 1 and 2, the human immunoglobulin light chain coding for antibody IDEC 131, the murine dihydrofolate reductase gene, and the human immunoglobulin heavy chain gene coding for antibody IDEC 131. This NEOSPLA vector was used in the first round of transfections during the development of the cell lines of the preferred embodiment of this invention. The NEOSPLA expression vector is substantially described in U.S. Pat. Nos. 5,648,267, 5,733,779, 6,017,733, 6,159,730, all four of which are incorporated in their entirety by reference herein.

A humanized anti-CD154 antibody (IDEC 131) is the desired high value protein produced by the embodiments of this invention as described herein. CD154 is a ligand for CD40, which is a cell surface molecule of immature and mature B lymphocytes, which when cross linked by antibodies, induces B cell proliferation. The anti-CD154 antibody has been substantially described in U.S. Pat. No. 6,001,358, which is incorporated in its entirety by reference herein.

An inducible promoter system is utilized in the preferred embodiment over a constitutive promoter in that it was considered possible that constitutive expression of anti-apoptotic genes could interfere with cell division over the long term, in a production cell line, which is required to grow continuously. It is entirely possible, however, that in some particular embodiments of this invention, constitutive expression of anti-apoptotic genes could be appropriate and desirable.

The vector pVgRXR (from Invitrogen, Carlsbad, Calif.), utilized in the preferred embodiments of the present invention, features an ecdysone-inducible expression system. Both subunits of a functional hybrid ecdysone steroid hormone receptor from Drosophila are constitutively expressed from the regulator vector pVgRXR, while the hybrid ecdysone-responsive promoter (p-Δ-HSP), which ultimately drives expression of the gene of interest, is located on a second steroid hormone inducible expression vector. Mammalian cells are first transfected with pVgRXR and then stable cell lines, presumptively expressing the functional hybrid ecdysone steroid hormone receptor are selected by exposure to Zeocin. In the presence of the inducer steroid, ponasterone A, the functional hybrid ecdysone steroid hormone receptor binds upstream of the hybrid ecdysone responsive promoter, thereby activating expression of the gene of interest. When steroid hormone is supplied to these cell lines their ability to stimulate transcription from a steroid hormone inducible promoter can be measured by transient transfection of an inducible expression vector with a readily measurable gene product such as beta galactosidase. Most of these stable Zeocin resistant cell lines will not induce a steroid responsive gene.

After establishing a modified cell line that stably expresses the hybrid steroid hormone receptor at a level sufficient to support steroid induction, a plasmid containing the gene of interest under the control of a steroid responsive promoter, as well as the dominant selectable marker gene for puromycin, is transfected into this cell line. Cell lines stably expressing the promoter are then derived by selection for puromycin. These cell lines are then assayed for their ability to induce the genes of interest when steroid hormone is provided. Most of these cell lines are not inducible by steroid. As noted supra, the steroid induction system has been substantially described by Evans in U.S. Pat. No. 5,534,418, which is hereby incorporated in its entirety by reference.

This ecdysone-inducible system was used in the second and third rounds, respectively, of the post-antibody IDEC 131 stages of development of the cell line embodiments of this invention. The second transfection step was the introduction of pVgRXR into the IDEC 131 cell line. The third transfection step was the introduction of an ecdysone-inducible genes, either with or without the gene for green fluorescent protein (GFP).

The Invitrogen expression vector pIND was modified so as to be able to accommodate up to three further genes of interest, and was additionally modified by the removal of the dominant selectable marker gene neomycin phosphotransferase and its replacement with the selectable puromycin resistance gene. In these subsequent rounds of transfection, modifications of the expression vector included embodiments carrying the Aven gene, the E1B-19K gene, and both genes together, in each case with and without GFP. Examples of such vectors are depicted in FIGS. 2 and 3. FIG. 2 depicts the modified Invitrogen expression vectors PX+E1B-19K; FIG. 3 depicts the modified Invitrogen vector PX+Aven+E1B-19K. Vectors such as these were used in the third round of transfections, to create cell lines expressing these two anti-apoptotic proteins, both singly, and in combination. When GFP is expressed in these CHO cells, in response to steroid induction, it provides a positive marker of protein expression, which is useful in sorting and selecting high-expressing steroid inducible cells by flow cytometry.

The detailed sequence listings for the Aven cDNA polynucleotide and Aven polypeptide amino acid sequences are shown in FIG. 4; sequence listings for the E1B-19K cDNA polynucleotide and E1B-19K polypeptide amino acid are shown in FIG. 5.

Example 2

Derivation of Cell Populations

Mammalian cells used in the commercial manufacture of therapeutic proteins, such as Chinese Hamster Ovary (CHO) cells, are immortalized cell lines which can continue to undergo continuous rounds of division, generation after generation, indefinitely. This stands in marked contrast to primary cultures of normal diploid animal cells, which have a finite lifespan that manifests as senescence and cessation of division at approximately 50 generations.

In general, the standard level of homogeneity of a cell line is achieved by having a cell population derive from a single cell. It is not considered to be absolutely provable that a population has a single cell ancestral source, but rigorous methods have been established which are accepted as creating a very high probability that this is the case. This procedure, known as single cell cloning, is accomplished by diluting suspended cells in culture medium to a point where, statistically, there is less than one cell in the unit volume which is aliquoted into a cell culture well. Visual and automated methods back up the statistical method to assure the presence of not more than one cell per culture well. As small populations emerge within these wells, they can thus be considered highly likely to be single cell derived. This approach is the one used in the development of cell populations used in examples 7 and 8, detailed below.

Another approach to obtaining a homogeneous cell population is to select a pool of cells, which are phenotypically homogeneous by criteria that can be measured by flow cytometry. Flow cytometry is a method that measures fluorescent or light scattering characteristics of individual cells, one by one, and on the basis of these measurements makes a decision to collect or to reject each cell. This is a powerful method that can create highly homogeneous pools of cells, which can then be expanded and banked as a particular population. However homogeneous this population may be, and it may be indistinguishable by any measure from a single cell-derived population as described above, it is not considered clonal, as defined by the single cell source standard. An advantage of this flow cytometric method is that large populations, homogeneous for desired features, can be obtained much more quickly than can populations that originate as single cells. This flow cytometry selection procedure is the one used in the generation of populations used in examples 5 and 6, below. The flow cytometry selectable feature was the expression of green fluorescent protein (GFP), as detailed below.

Example 3

Cell Line History

The CHO 5C11 cell line, the immediate parent of the cell lines described in this invention, has two features significant features that support the expression of the anti-apoptotic genes and demonstration of the inventive method and preferred embodiments described herein. The parent cell line secretes a desired protein, antibody IDEC 131, and it expresses a cytosolic hybrid ecdysone steroid hormone receptor, which is a component of a system whereby expression of anti-apoptotic genes is induced.

The CHO 5C11 cell line originates from the Chinese Hamster Ovary cell line, CHO DG44, developed at Columbia University (Urlaub, PNAS 83 (17): 6519-23 (1986)). The CHO DG44 line is deficient in its expression of dihydrofolate reductase (DHFR), and is thus dependent on the expression of a transfected DHFR in order to acquire a resistance to methotrexate, a toxic agent used to select for genomic amplification. In the development to its present state, the CHO 5C11 line has undergone two major transfection events since the DG44 stage of its development.

The first transfection of the CHO DG44 line was with the NEOSPLA vector containing the coding sequence for an antibody, IDEC 131. Selection in neomycin was performed under conditions in which populations are likely to have been derived from a single cell, and antibody-producing cell lines were expanded. One of the resulting high producing neomycin-resistant cell lines, G418, was selected for further development.

The antibody producing G418 cell line was subjected to further selective pressure and antibody-expression amplification by growth in stepwise increasing methotrexate at concentrations of 5 nM, 50 nM, and finally 500 nM, each step conducted under selection conditions in which populations are likely to have been derived from a single cell to yield a cell line, identified as 500E9.

In a second transfection step, this 500 nM methotrexate-resistant cell line was transfected by electroporation with the vector pVgRXR and selected in Zeocin (from Invitrogen Corp., Carlsbad, Calif.), which confers a steroid-inducible expression system in the host cell. The resulting post-transfection Zeocin-resistant cell lines were selected under conditions in which cell lines are likely to have been derived from a single cell. These individual cell lines were then tested for inducibility by transient transfections with a steroid inducible beta-galactosidase gene, to yield the steroid-receptor inducible cell line, CHO 5C11. The cell line CHO 5C11 has a single integration site of the plasmid pVgRXR, reinforcing its probable derivation from a single cell.

In a third transfection step, the CHO 5C11 line was then used as a parent for the series of transfected lines used in the inventive examples disclosed herein. The Invitrogen vector system was modified to allow the further expression of up to three further separate genes and the introduction of the dominant selectable marker for puromycin resistance. Accordingly, six vectors systems were constructed containing, respectively (1) green fluorescent protein (GFP), (2) GFP+Aven, (3) GFP+E1B-19K, and (4) GFP+Aven+E1B-19K (5) E1B-19K, and (6) Aven+E1B-19K. GFP is a fluorescing marker protein, the expression of which allows selection by a flow cytometry. Aven and E1B-19K are the genes for the two above described anti-apoptotic proteins.

In the case of the plasmids containing GFP, post-transfection cell populations were first grown under puromycin-selective pressure to yield stable protein-expressing pools of the various transfected populations. The ability of each of these populations to express the transfected genes in response to steroid induction was tracked by monitoring the expression of steroid-induced GFP in a flow cytometer, and highly fluorescing cells were positively selected and pooled by flow cytometry. Expression of the other newly transected genes was verified by Western-blot studies of cell lysates. This approach yields a cell population that is homogeneous with regard to rates of protein expression, but the population is not derived from a single cell.

In another approach, cells derived from transfections and puromycin-selected for stable transformation with a vector containing E1B-19K (number 5, as listed above) and with a vector containing E1B-19K and Aven (number 6, as listed above) were isolated into potentially single cell cultures and expanded to the point whereby highly inducible populations could be identified. Such potentially single-cell-derived populations were then expanded by serial culture, and ultimately used in experimental examples 3 and 4, as detailed below.

Example 4

Cell Culture Systems and Media

The CHO 5C11 line has been grown in a serum-free medium CHO SSFM II, a Gibco product (Grand Island, N.Y.). Cell cultures are grown continuously by sequentially passing a portion of a high cell density culture to a new culture with fresh medium. In experimental examples 7 and 8, as detailed below, a glucose-free variant of the serum-free CHO SSFM II medium Was used. Experimental studies, using batch or terminal cultures, have been conducted in small-scale systems, such as cell culture dishes, containing culture volumes of 1 to 2 ml, and spinner flasks, containing cultures of 50 to 200 ml in volume.

The practice of this invention can be applied to a wide variety of cell types, culture systems, and culture media. In general, commercial culture systems include bioreactor vessels with volumes that range between 1 and 50,000 liters. Cells, in general, are grown in free suspension, but examples of attachment-dependent and aggregated cells are also common. Numerous references address means for large scale cultures and related considerations; an exemplary reference is R. J. Freshney, Animal Cell Culture" A Practical Approach, $2^{nd}$ Ed., Oxford University Press, New York, 1992 and M. Butler, Mammalian Cell Biotechnology: A Practical Approach, Oxford University Press, New York, 1991. A representative reference detailing cell culture medium considerations is the ATCC Media Handbook, Cote al. al., published by the American Type Culture Collection, Rockville, Md., 1984.

Example 5

In this study, depicted in FIG. 6, the survival of cells (1) transfected with GFP alone, (2) with GFP and Aven, (3) with GFP and E1B-19K, (4) with GFP and the combination of Aven and E1B19K, and (5) non-transfected parental cells was compared in 3 day cultures, in cell culture dishes. Cells were grown in normal medium, i.e., CHO SSFM II, until the initiation of the experimental culture, whereupon the medium was changed to a glucose-free medium, and induction of transfected genes effected by the addition of 5 µM ponasterone A. The glucose-free environment subjects cells to a critical nutrient crisis, and thus creates a strong apoptotic stimulus.

By the conclusion of day 1 in the glucose-free environment, all cultures, which had an initial viability of 95%, have suffered a loss in viability, but the viability of Aven+E1B-19K culture has dropped to 80%, while all other cultures have dropped to approximately 70%. The Aven+E1B-19K culture continues to show significantly higher viability over other cultures over the next two days. At the conclusion of day 2, a significant difference in viability has emerged between the two cultures representing E1B-19K-transfection and the Aven-transfection vs. the two control cultures, represented by the GFP (alone) and the non-transfected parental line. Thus, on day 2, the viability of the Aven+E1B-19K culture stands at 80%, the viability of the Aven and the E1B-19K cultures both stand at approximately 60%, while the control cultures stand at 30% to 40%. By day 3, the Aven+E1B-19K culture stands at 75% viability, the E1B-19K culture stands at 45% viability, and the Aven culture and both control cultures show zero viability.

These data show that the expression of each gene, E1B-19K alone and Aven alone, has an anti-apoptotic effect in CHO cells stressed by nutrient deprivation, and that the effect of the expression of E1B-19K alone is considerably greater than that of Aven alone. The effect of the two genes, E1B-19K and Aven, together is synergistic with respect to their individual effect, i.e., the effect of combined expression is greater than the simple addition of their individual effects. The latter conclusion is supported by the observation that while Aven alone appears to offer no survival margin benefit on day 3, its expression in combination with E1B-19K confers a 20% greater survival margin over the cells expressing E1B-19K alone.

Example 6

In this study, depicted in FIG. 7, the performance of cells (1) transfected with GFP alone, (2) transfected with GFP and Aven, (3) transfected with GFP and E1B-19K, (4) transfected with GFP and the combination of Aven and E1B19K, and (5) non-transfected parental cells was compared. Each of the five cell types was cultured in the presence and absence of ponasterone A, thus creating a total of 10 experimental groups.

Two days before the initiation of the test spinner cultures, 5 µM ponasterone A was added to the media of cells which were to have the steroid present during the experimental period, in order to have full induction of the anti-apoptotic genes. Each experimental culture was initiated by seeding 250K cells/ml in spinner flasks in normal glucose-containing medium. At day 2, the medium was changed to glucose-free medium, and the culture continued.

For ease in visualizing the data, results from the experiment are distributed into five graphs showing viability as a function of days in culture.

FIG. 7a shows the precipitous loss of viability that occurs by day 2 in the control GFP-alone cultures, with and without ponasterone A.

FIG. 7b shows the Aven cultures, with and without ponasterone A, and that the presence of the ponasterone (which induces Aven expression) does have an effect in increasing the survival of a small percentage of cells through the third day of culture.

Figure 7C:
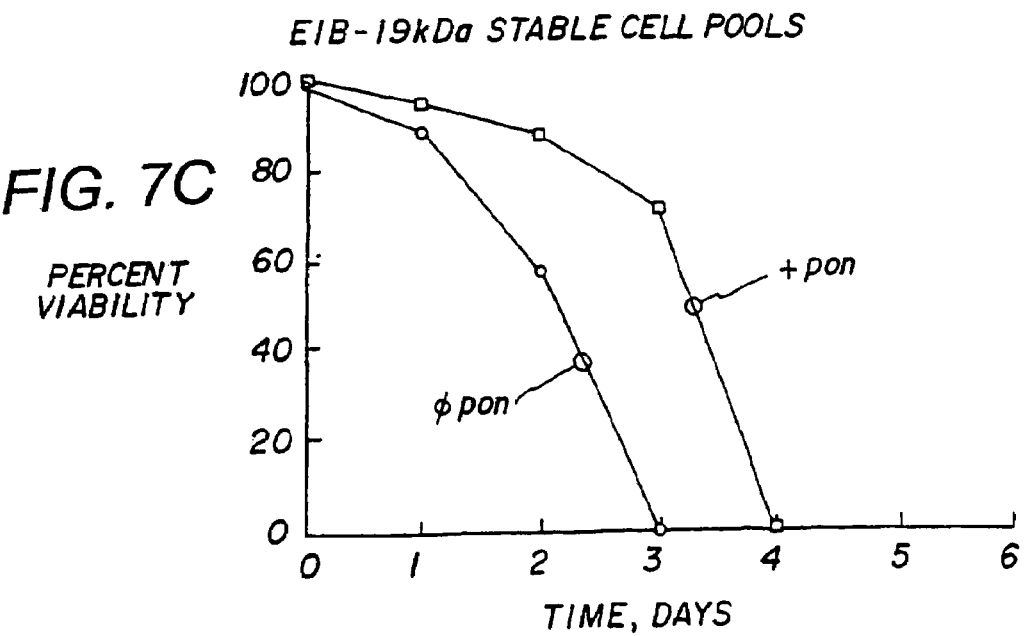

FIG. 7c shows the E1B-19K cells, with and without ponasterone A, and that the viability of both cultures is significantly greater than that of controls (FIG. 6a) and Aven alone (FIG. 6b), and that the presence of the steroid effects a markedly increased survival.

FIG. 7d shows the E1B-19K+Aven cells, with and without ponasterone A. The viability of these cells in the presence of ponasterone extends is at 80% on day 3, when all other cultures have already completely failed, and it is not until well into the fifth day of culture that viability drops to zero.

FIG. 7e focuses on the two most disparate groups for the purpose of a head-to-head comparison, the GFP control group, showing poor viability and the E1B-19K group, showing very high viability; each of the two cell types in the presence of ponasterone.

These data confirm the results of example 1 in that expression each of E1B-19K alone and Aven alone has an anti-apoptotic viability-increasing effect, that the effect of E1B-19K alone is very significant and greater than that of Aven alone, and that the expression of the two genes in combination yields a synergistic effect, i.e., a result larger than that which would be expected from the addition of the individual gene effects. That the anti-apoptotic effects are specifically linked to the expression of these transfected genes is further supported by the observation that the effects are entirely dependent on the steroid induction.

Example 7

Figure 8:
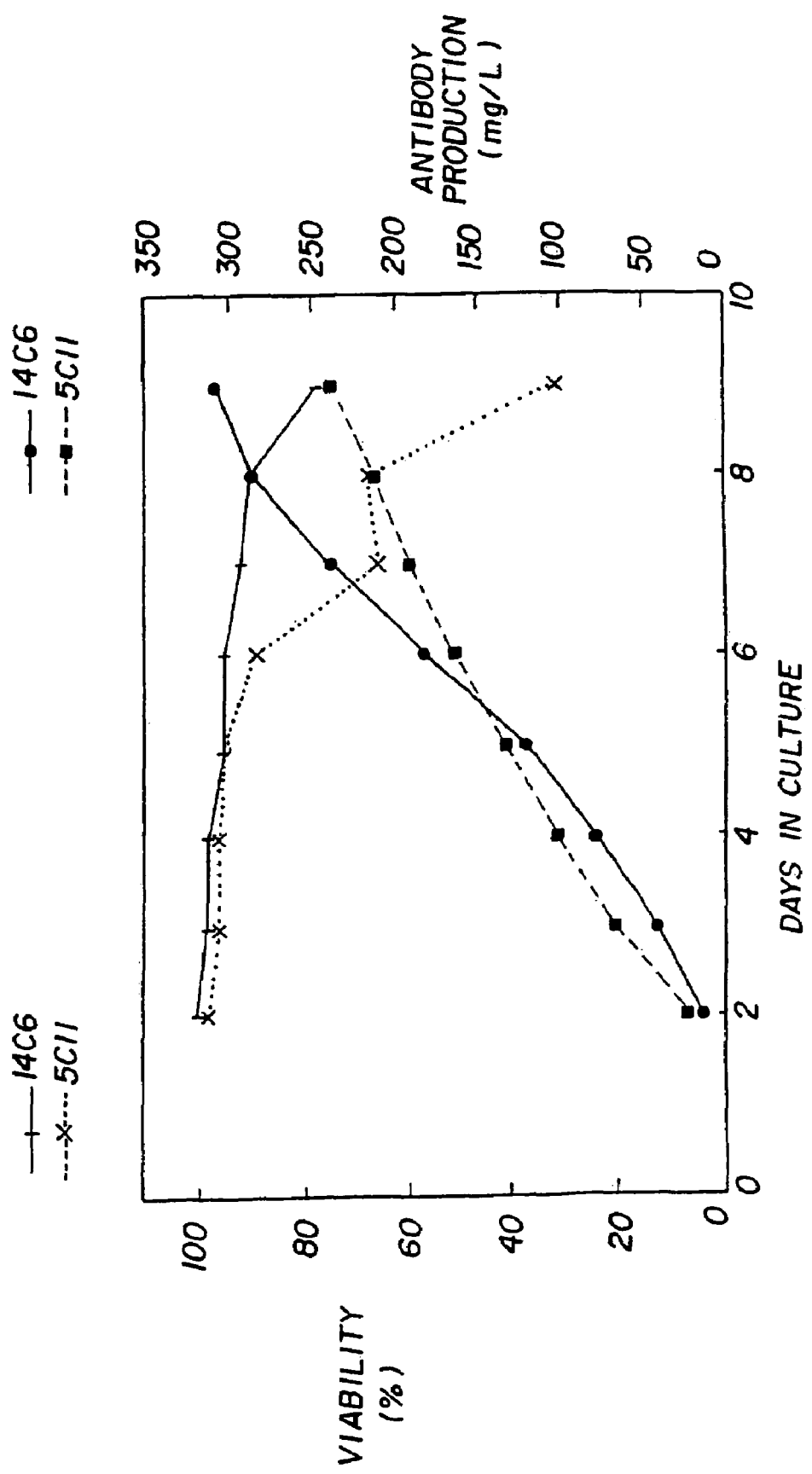
FIG. 8 depicts data with respect to inducible expression of anti-apoptotic polypeptides: comparing the batch culture performance of steroid-induced cells expressing E1B-19K and Aven to the non-transfected CHO cell line with respect to viability and antibody production level.

This study, depicted in FIG. 8, involved the comparison of the performance of the stable cell line transfected with both E1B-19K and Aven vs. the performance of parent 5C11 line, as a control, with regard to both cell culture growth and antibody production. The transfected cell line (E1B-19K and Aven ) in this example, as well as in example 4, was derived by single cell cloning following the transfection.

Spinner flask cultures were seeded at $3 \times 10^5$ cells/ml and grown as batch culture for 9 days. The steroid ponasterone at 5 µM, a concentration, which effectively induces the transfected steroid-inducible genes, was added to both cultures. Culture samples were withdrawn daily to obtain cell counts and for antibody concentration measurements by ELISA.

The data show the cultures to have very parallel performance until day 6. On day six narrow differences are apparent in that the viability of the control culture has fallen slightly below that of the E1B-19K+Aven culture, and the antibody titer of the E1B-19K+Aven has increased slightly above that of the control culture. Over the next three days these differences became progressively larger. By day 9 the viability of the control culture has fallen to 28%, while the E1B-19K+Aven culture has a 78% viability. The final titer of the control culture was 247 mg/L, while that of the E1B-19K+Aven culture has reached 309 mg/L, an increase of approximately 20%.

Example 8

Figure 9:
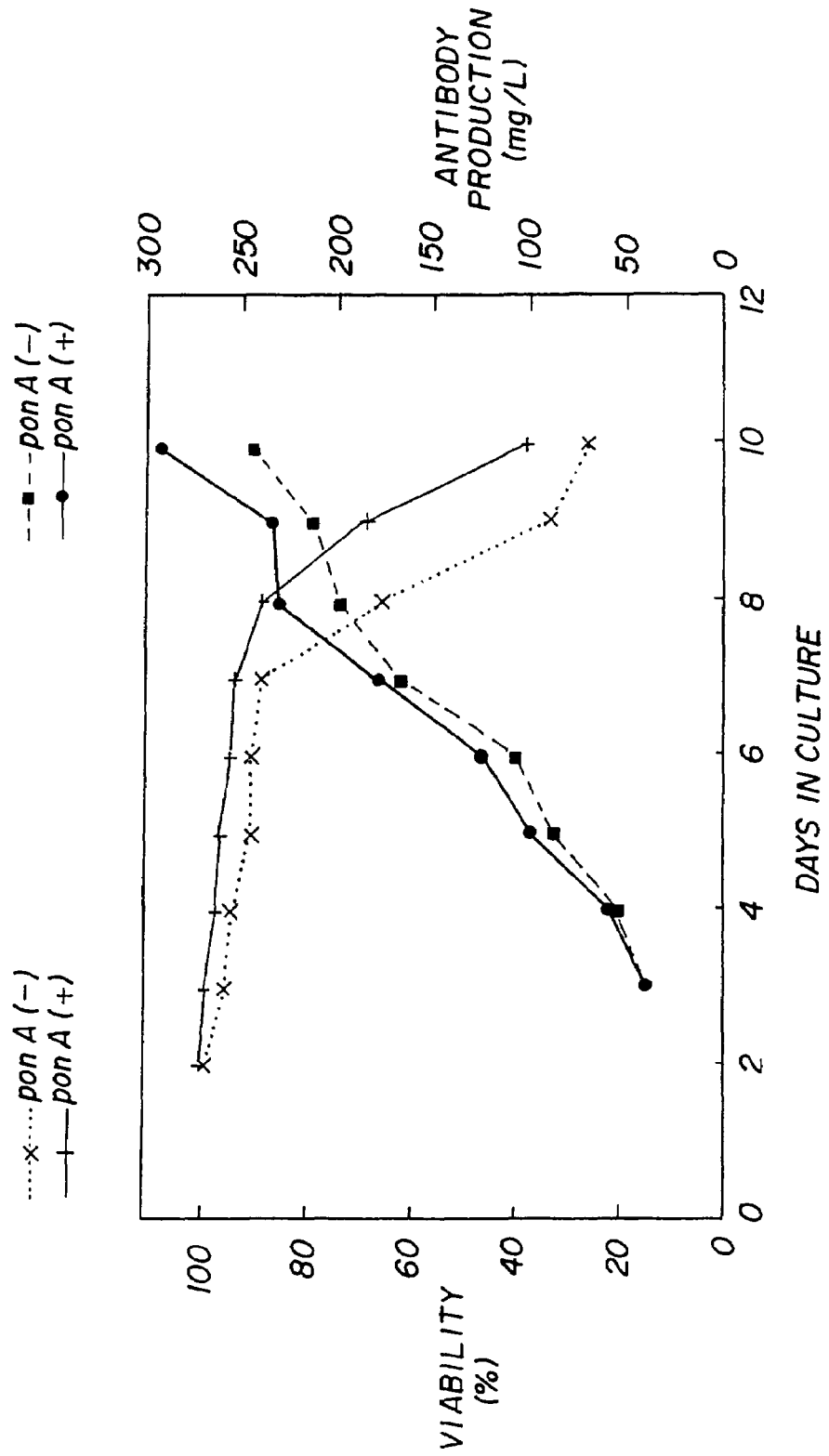

This study, depicted in FIG. 9, represents a test of the effectiveness of the steroid induction in the cell line stably transfected with E1B-19K plus Aven. Thus, two cultures of E1B-19K plus Aven cells were seeded at 300K cells/ml; 5 µM ponasterone A was added to one (experimental) culture on day two, while the other (control) culture received no steroid. The two cultures showed very parallel performance during the first 6 days of culture, with the steroid-induced culture showing but marginally better viability. By day 8, viability of the control culture had dropped to 60% while the steroid-induced cell line remained 90% viable. On day 9, viability of the control culture was 35% while the steroid-induced culture was 70%. Finally, on day 10, the control culture was 30% viable, while the induced cell line was 40% viable. The final titer of the control culture was 240 mgs/liter, while the final titer of the steroid-induced culture was 290 mgs/liter, an increase of approximately 20%.

Examples 7 and 8 are cases in which the apoptotic stress is that of the nutrient depletion and toxicity build up over the course of a batch culture extending over a nine to ten-day period. Apoptosis manifests as the precipitous die off of cells which begins, in the case of control cells, around the $6^{th}$ or $7^{th}$ day of a batch culture. The conclusion of the first two examples, together, is that the combined effect of the expression of transfected anti-apoptotic genes E1B-19K and Aven is to extend the life time of the cultures, to increase the culture antibody titer by approximately 20%, and that the activity of these two gene are indeed dependent on the steroid induction.

Example 9

Other Protein Therapeutic Product Examples

The foregoing examples, representing one embodiment of this invention, pertain to the production of a humanized anti-CD154 antibody (IDEC 131). CD154 is a ligand for CD 40, which is a cell surface molecule of immature and mature B lymphocytes, which when cross-linked by antibodies, induces B cell proliferation.

Preferred examples of therapeutic protein products, particularly antibodies, and the manufacture thereof by mammalian cell fermentation processes toward which those skilled in the art could apply this inventive method are as follows:

Antibodies to human RSV fusion protein, as described in U.S. Pat. Nos. 5,811,524, 5,840,298, 5,866,125, 5,939,068, 5,955,364, and 5,958,765.

Antibodies to human CD20, designed for the treatment of B cell lymphoma, as described in U.S. Pat. Nos. 5,736,137 and 5,776,456.

Chimeric recombinant antibodies, including an old world monkey portion and a human portion, for human therapy, as described in U.S. Pat. Nos. 5,658,570, 5,681,722, 5,693,780, 5,750,105, and 5,756,096.

Antibodies to human CD23, monoclonals containing human gamma 1 constant domains, which inhibit IL-4 induced IgE production by B cells, as described in U.S. Pat. No. 6,011,138.

Primatized antibodies against human B7.1 (CD80) and B7.2 (CD86), useful as specific immunosuppressants in the treatment of autoimmune diseases and the prevention of transplant rejection, as described in U.S. Pat. No. 6,113,898.

Chimeric antibodies against human CD4 gamma 1 constant domains, containing old world monkey variable sequences and human constant domain sequences, as described in U.S. Pat. No. 6,136,310.

Example 10

Aven Enhances the Function Of Bcl-$x_L$ Following Serum Deprivation

Many mammalian cells require serum to proliferate in culture unless they have been adapted to grow in serum-free environments. Serum provides cells with growth factors, nutrients, metabolites, hormones, and cytokines and has been shown to provide anti-apoptotic effects during bioreactor cultivation. We have shown that CHO-K1 to undergo apoptosis following serum deprivation (FIG. 10 and Mastrangelo et al., Bioreg. Bioeng. 67 (5): 544-54 (2000), Figueroa et al., Bioreg. Bioeng. 7(3):211-222 (2001)). Since the depletion of nutrients and growth factors can occur during the production of biological products, serum deprivation studies were initiated as a model for this environment in cell culture.

Figure 11A:
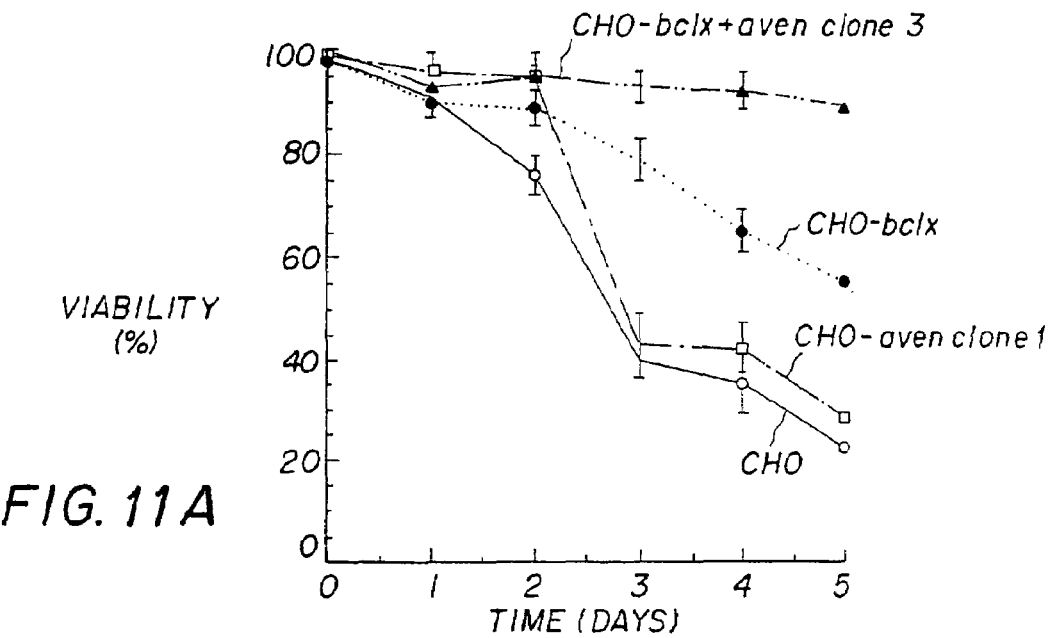
FIGS. 11a and 11b contains cell viability data relating to CHO cells cultured in 10% FBS that express Aven, Bcl-$x_L$, and Bcl-$x_L$+Aven subsequently culture i.e., exposed to serum-free medium.
Figure 11B:
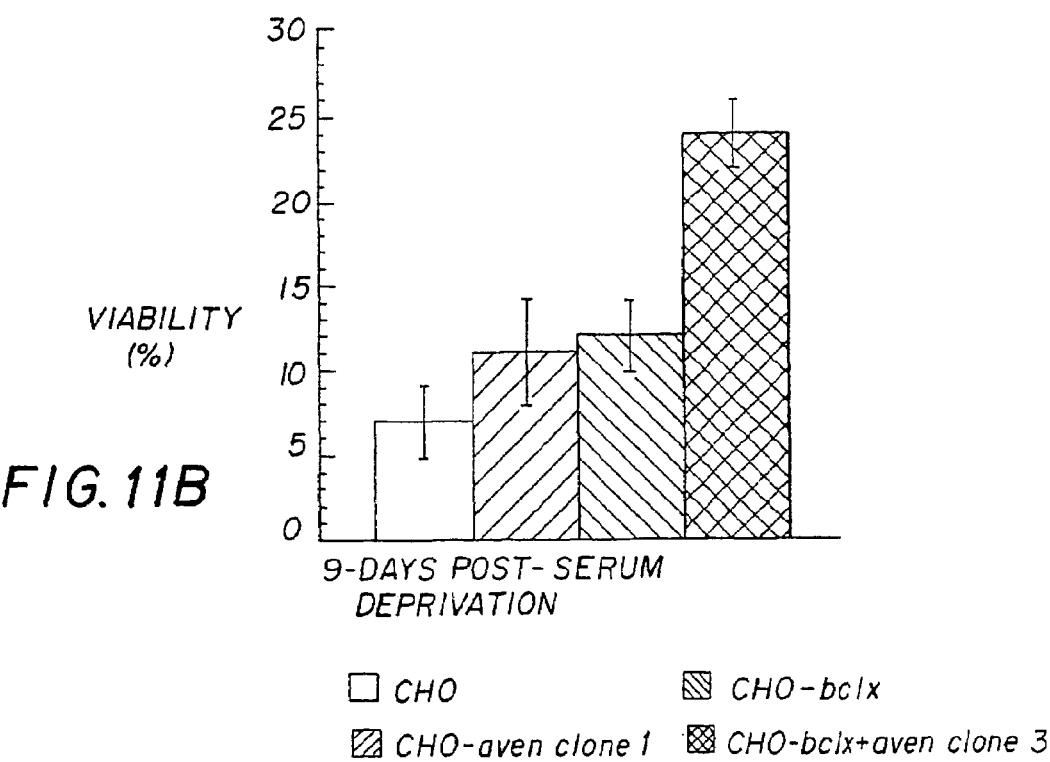

In order to determine if cells could be engineered to overcome this insult, CHO cells grown in 10% FBS and expressing Aven, Bcl-$x_L$, and Bcl-$x_L$+Aven were subsequently exposed to serum-free medium. Viability was then monitored at multiple days post deprivation, as shown in FIG. 11A. The engineered cell lines were observed to outperform the parental CHO K-1 cells by 2-days post serum deprivation. Aven expression provided protection during the first 2 days following serum deprivation and allowed the culture to maintain viability greater than 90% at this time. In fact, the viability of the CHO-aven cells was higher than that of the CHO-bcl-$x_L$ at 2 days withdrawal and comparable to that of CHO-bcl-$x_L$+ aven. However, the protection offered by the expression of Aven was minimal after 2-days post serum withdrawal when compared to the protection offered by Bcl-$x_L$. Overall, CHO-bcl-$x_L$+aven outperformed CHO-bcl-$x_L$, CHO-aven and the parental CHO K-1. The enhanced protection offered by the combination of Aven and Bcl-$x_L$ was apparent by 3-days post serum deprivation and sustained for 5 days following exposure to serum free medium. CHO-bcl-$x_L$+aven maintained a viability greater than 85% viability; whereas, the CHO-K1 viability was just over 20% and CHO-bcl-$x_L$ displayed a viability of less than 60% at this same time. A viability measurement was also taken at 9 days post-withdrawal to see if the protection was sustained for extended periods (FIG. 11B). At 9-days post-serum deprivation, the parental CHO-K1 cells viability was 7% viability and the cell expressing one anti-apoptotic gene had viabilities slightly above 10%. However, the CHO-bcl-$x_L$+aven maintained viability of 24%, which was double that of the cell expressing only one gene and three-fold higher than the control.

Example 11

Aven Enhances the Function of Bcl-$x_L$ Under 4- and 5-Day Spent Medium

Figure 10:
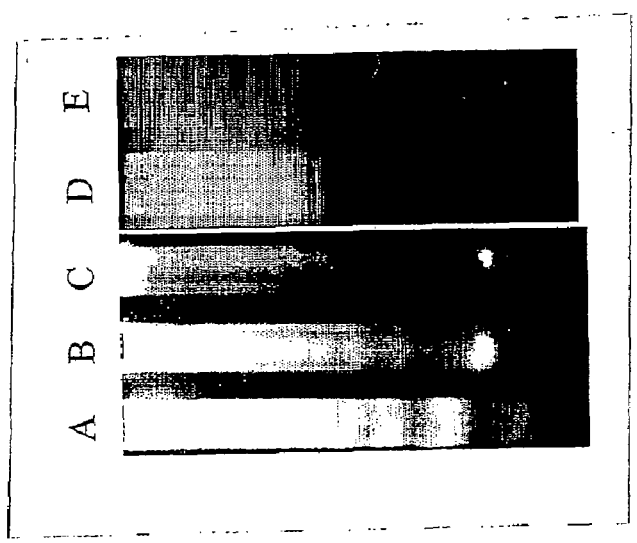
FIG. 10 contains results which indicate that a CHO cell line (CHO-K1) undergoes apoptosis following serum deprivation and spent medium.

The accumulation of metabolic waste products and cellular cytosolic debris, along with the depletion of nutrients and growth factors, is often encountered toward the end of many bioreactor runs and may create an environment unfavorable for cell survival. In order to model such an environment, CHO cells were exposed to medium from 4- and 5-day cultures and the effects of expressing Aven, Bcl-$x_L$ and Bcl-$x_L$+Aven were evaluated. In order to generate the spent medium, CHO K-1 cells were passaged and expanded in DMEM complete medium for 4- or 5-days prior to medium collection. A significant difference between 4- and 5-day spent medium was observed in the viability of the cells at collection time. Following 4-days of CHO K-1 expansion, the medium (yellow/orange color) was acidified by the accumulation of metabolic waste products, depletion of serum (buffering solution properties), and culture autocrine signals, however, the culture remained viable (greater than 75% viability) but was 100% confluent. After 5-days of culturing, CHO K-1 viability had diminished severely to below 30% viability and the cells were completely detached from the flask accompanied by further acidification of the culture medium (strong yellow color). The continued acidification of the medium is likely to be attributable primarily to the presence of a large percentage of cell death and lysis and the release of the cellular contents into the medium. As shown in FIG. 10, the exposure of CHO cells to 4- and 5-day spent medium culture conditions induced apoptosis.

Figure 12A:
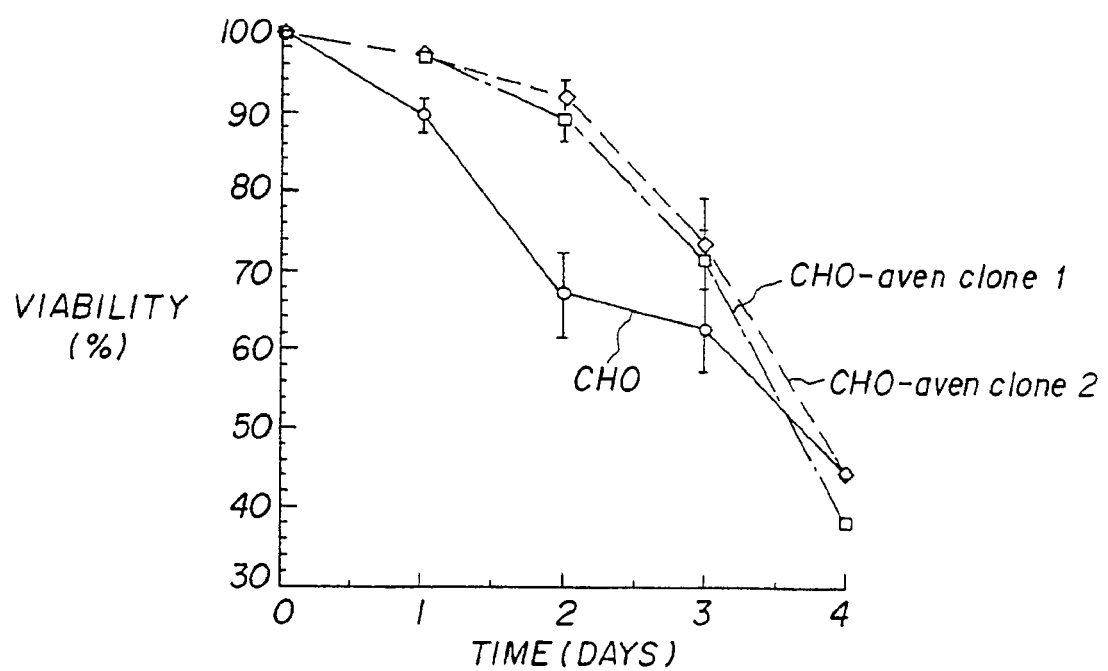
FIGS. 12a, b and c also contain viability data wherein CHO cells that express Aven, Bcl-$x_L$, and Bcl-$x_L$+Aven are cultured to serum free medium and cell viability measured after such culturing.
Figure 12B:
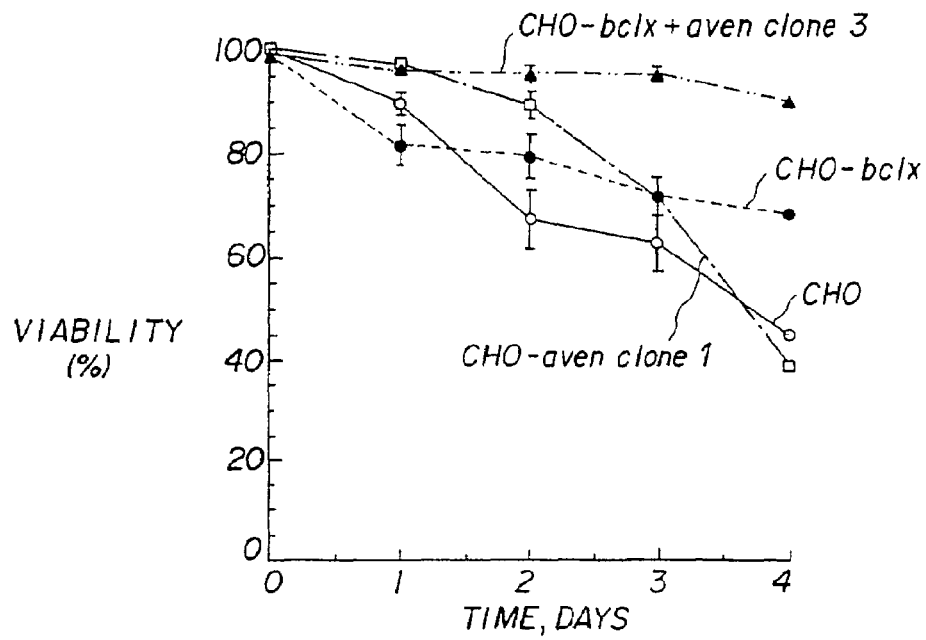

In order to examine cell viabilities in spent medium, cells were washed twice with PBS to ensure removal of serum and then exposed to spent culture medium. Following exposure to 4-day spent medium, engineered CHO K-1 cell lines displayed higher viabilities than the parental CHO K-1 (FIGS. 12A and 12B) at almost all time points. The expression of Aven alone enhanced viabilities for 3-days post exposure at which point viability dropped to a level comparable to parental CHO K-1 levels (FIG. 12A). To determine if this was a characteristic of the clone or the expressed gene, two different CHO-aven clones were exposed to the 4-day spent medium. Interestingly, both clones demonstrated the same characteristic pattern of protection in which viability was enhanced for the first three days and then declined to the level at or below wild-type CHO cells. In contrast, the CHO cells expressing Bcl-$x_L$ showed a different pattern of sensitivity to the 4-day spent medium (FIG. 12B). At 1-day post exposure, CHO-bcl-$x_L$ had the most significant drop in viability when compared to the other cell lines including the CHO-K1. By 2-days post exposure, CHO-bcl-$x_L$ viability had stabilized and expression of Bcl-$x_L$ offered protection compared to parental CHO-K1 for the duration of the exposure to spent medium. The viability of CHO-bcl-$x_L$+aven was equal to or better than CHO-aven, CHO-bcl-$x_L$ and parental CHO K-1 at all days exposure to 4-day spent medium. The cell line carrying two anti-apoptosis genes maintained a viability greater than 85% throughout the duration of the 4 day exposure to 4-day spent medium, while the viability of the parental CHO-K1 and CHO-aven was approximately 40% at this same time point.

Figure 12C:
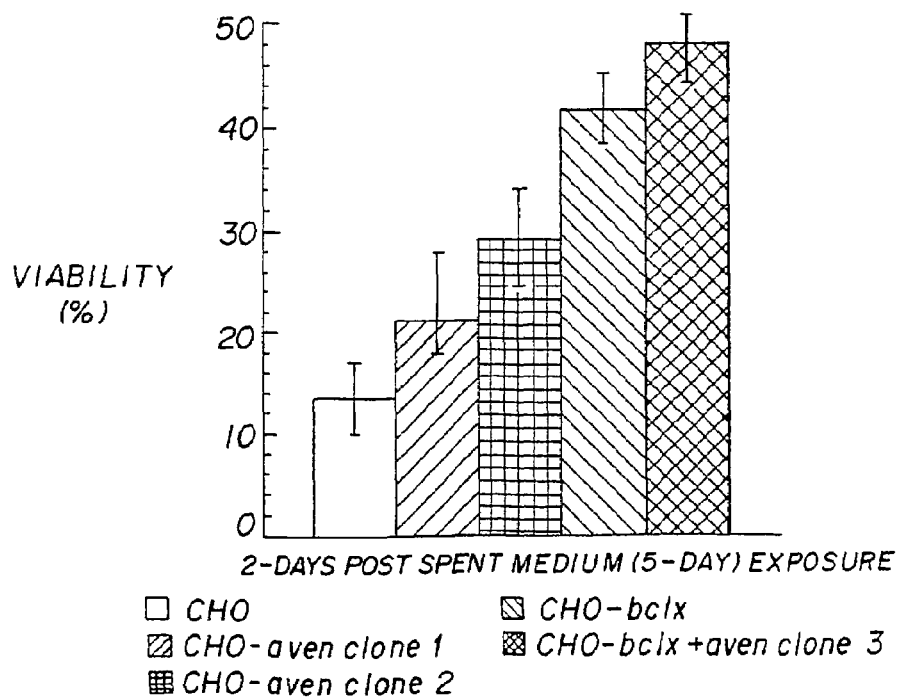

Cell death rates were significantly increased following exposure to 5-day spent medium as compared to that in 4-day spent medium. Cell culture viability for cells exposed to the 5-day spent medium dropped severely following 2-days exposure as shown in FIG. 12C. While the viability of the CHO-K1 was at 68% in 4-day spent medium, the level had dropped precipitously to 14% as a result of the increased toxicity of the 5-day medium. Once again, however, the engineered CHO cell lines outperformed parental CHO K-1. The expression of Aven in two different clones offered some protection against programmed cell death induced by exposure to 5-day spent medium when compared against the parental CHO K-1. Expression of Bcl-$x_L$ offered even more protection against the toxicity with a viability that exceeded 40% in the 5-day spent medium. The rate of cell death following exposure to 5-day spent medium was altered the most by the co-expression of Bcl-$x_L$ and Aven with a viability of 48% after 2 days in the environment. However, the enhanced protection offered by the expression of two genes over Bcl-$x_L$ alone was not as great in the more toxic 5-day spent medium as observed previously in the 4-day medium. The viability of the CHO-bclx$_L$+aven was consistently nearly 20 percentage points higher than CHO-bclx$_L$ in 4-day spent medium whereas the difference was less than 8 percentage points in the highly acidified and toxic 5-day spent medium.

Example 12

Additional Deprivation Studies Using Ecdysone Inducible Expression System

Figure 13A:
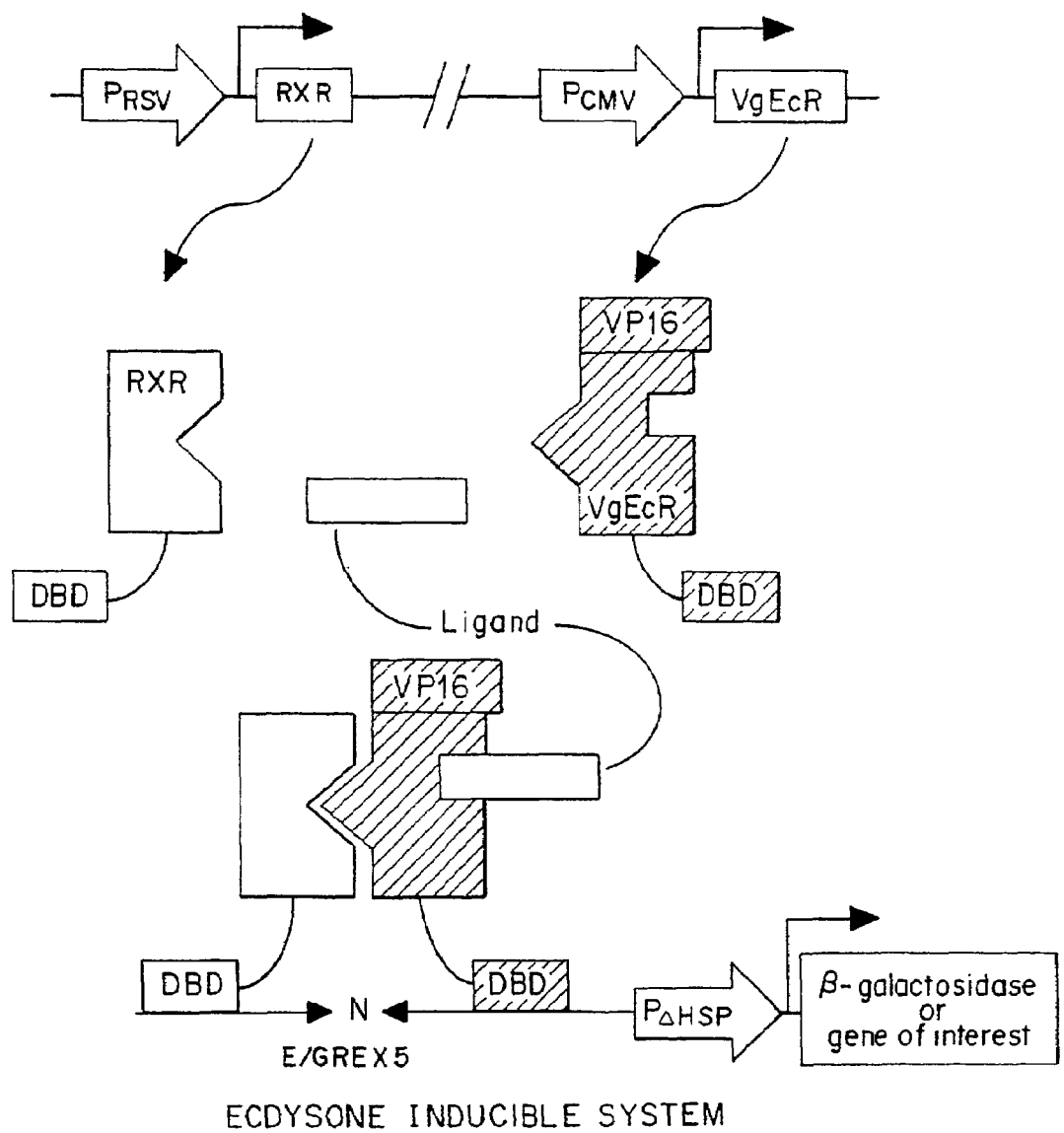
FIGS. 13a, b and c depict the inducible expression system utilized in the examples.
Figure 13B:
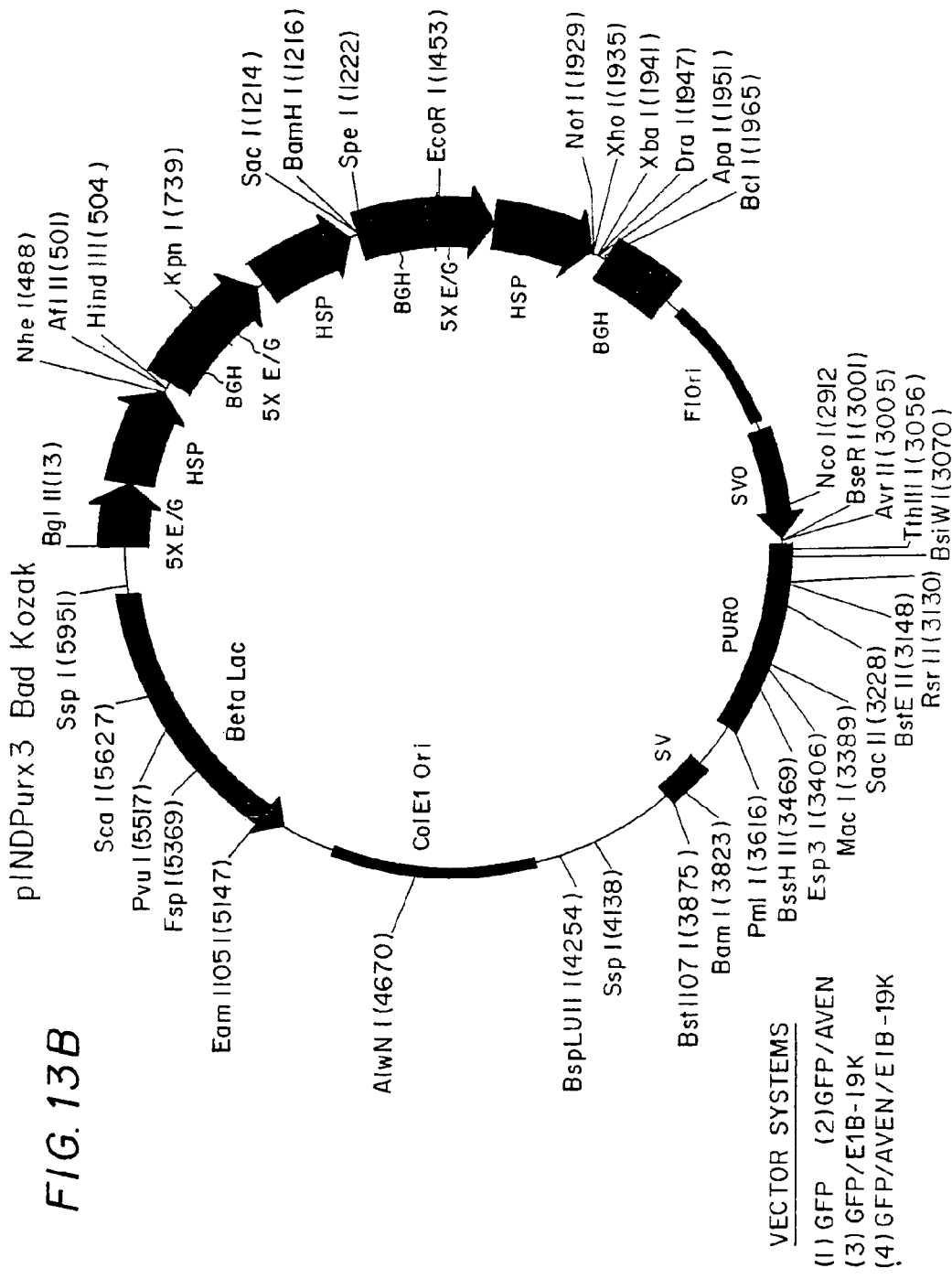
Figure 13C:
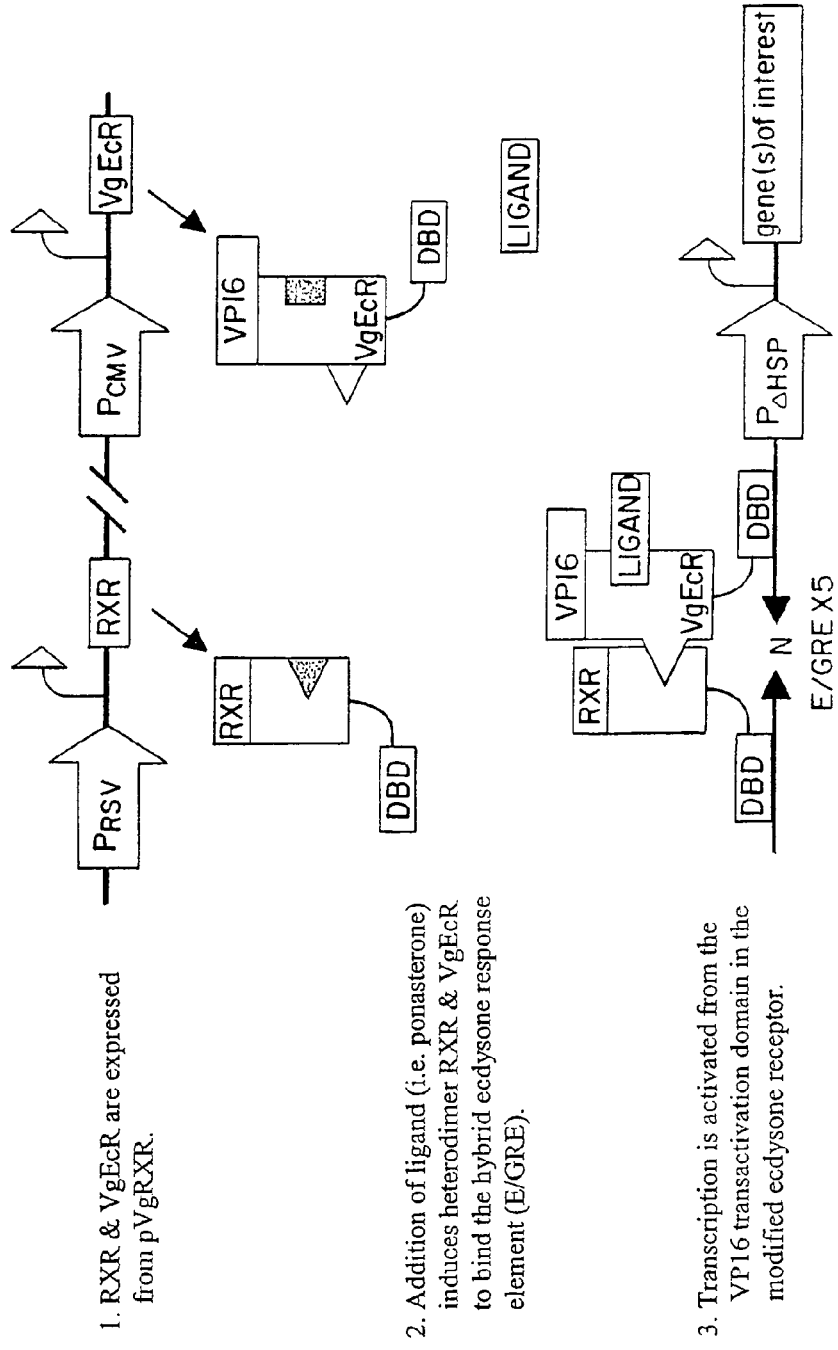

The ecdysone inducible system and vector systems used in this example and described previously are depicted schematically in FIGS. 13a & 13b respectively. As further shown in FIG. 13c, RXR and VgEcR are expressed from pVgRXR, and the addition of a ligand (i.e., ponasterone A) induces heterodimer RXR and VgEcR to bind to hybrid ecdysone response element (EGRE) with transcription activated from the VP16 transactivation domain in the modified ecdysone receptor.

As shown in FIG. 14, CHO cells containing this inducible expression system that express α-GFP, α-Aven or α-E1B-19K were induced with 5 µM ponasterone A.

Figure 15:
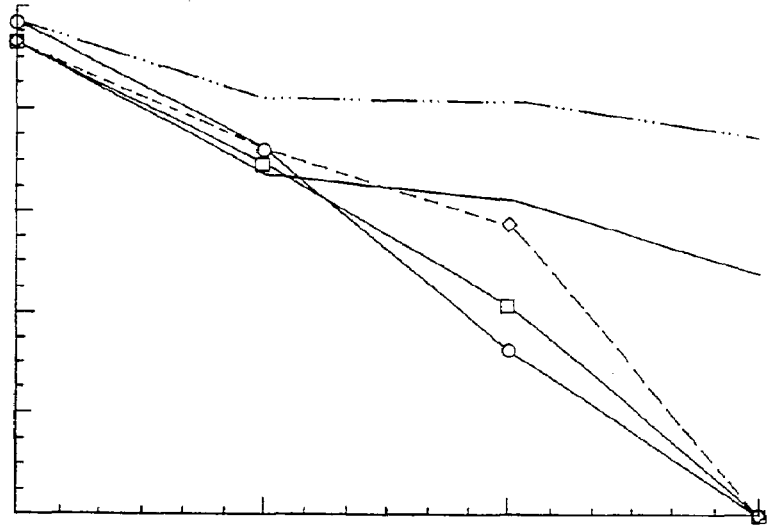
FIG. 15 contains glucose deprivation experimental results using 6-well cultures.
Figure 16:
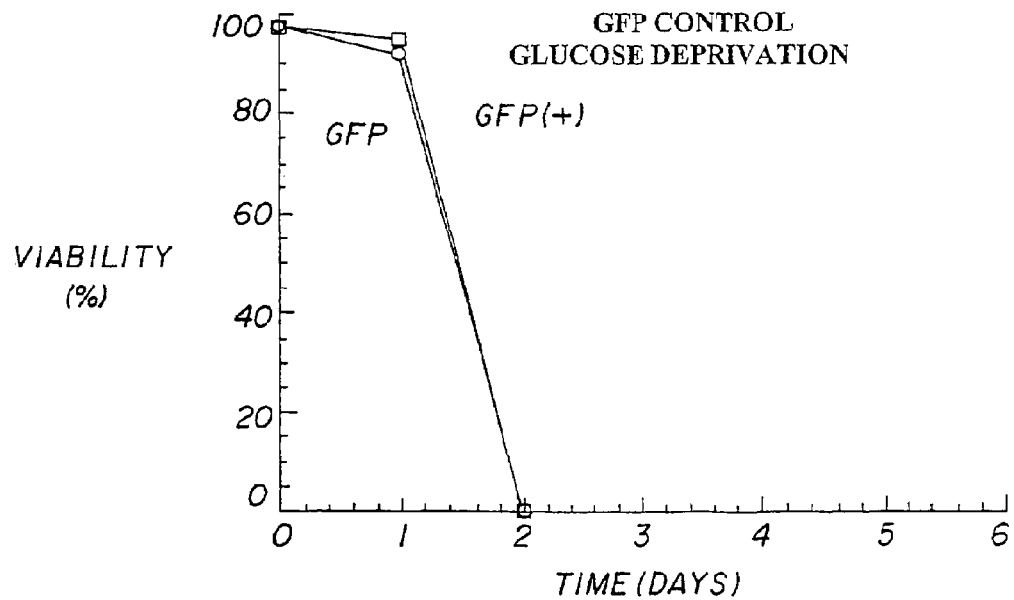
FIGS. 16-21 contain the results glucose deprivation experiments conducted in spinner flask cultures.
Figure 17:
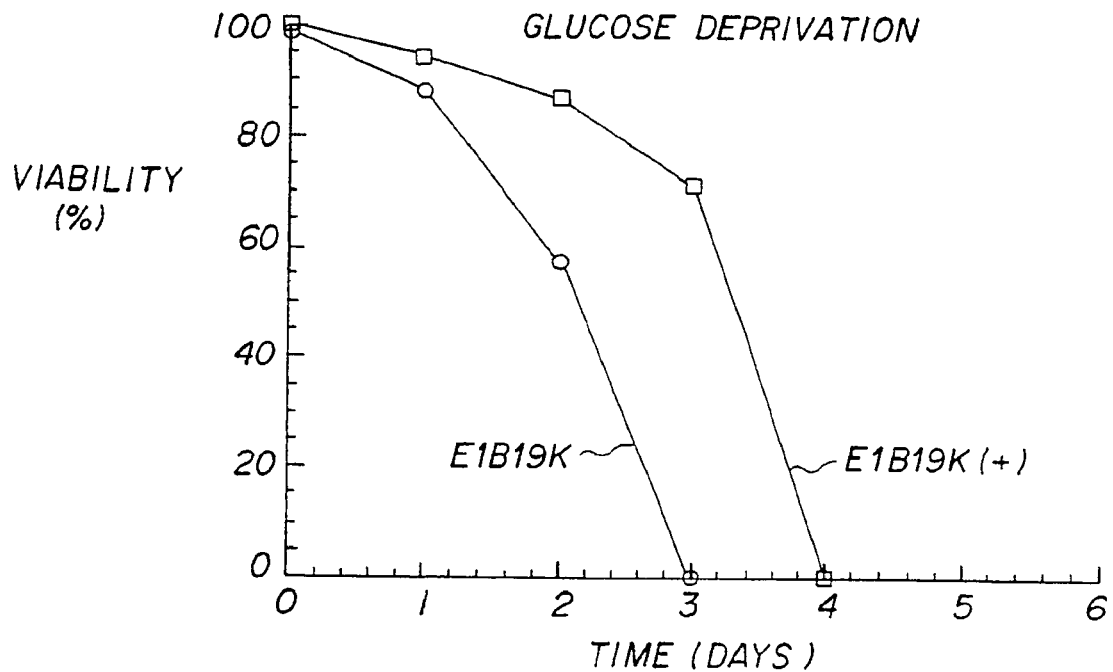
Figure 18:
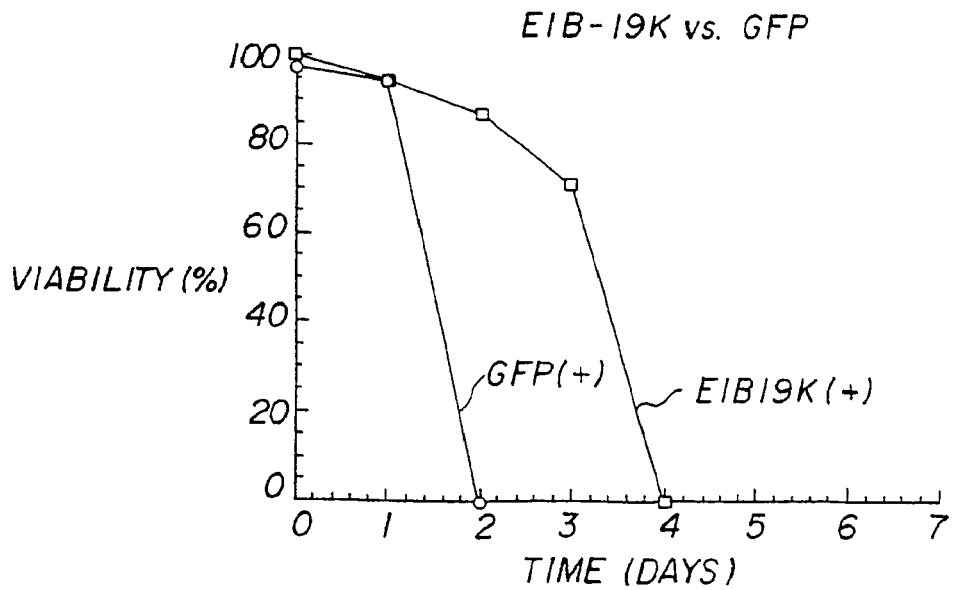

As shown in FIG. 15 glucose deprivation experiments were conducted using this inducible expression system (wherein cell populations in 6-well cultures were induced with 5 µM ponasterone for 48 hours before the start of the experiment) and cell viability measured over time. FIG. 16 contains spinner flask results for the GFP control group, FIG. 17 for cells that express E1B-19K, and FIG. 18 contains results comprising cell viability of cells that express E1B-19K vs GFP under glucose deprivation conditions in spinner flasks.

Figure 19:
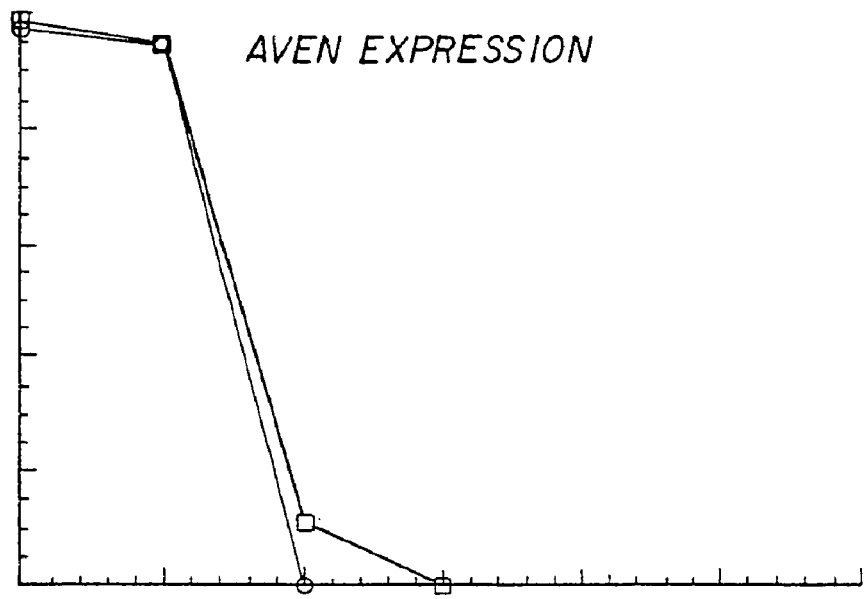
Figure 20:
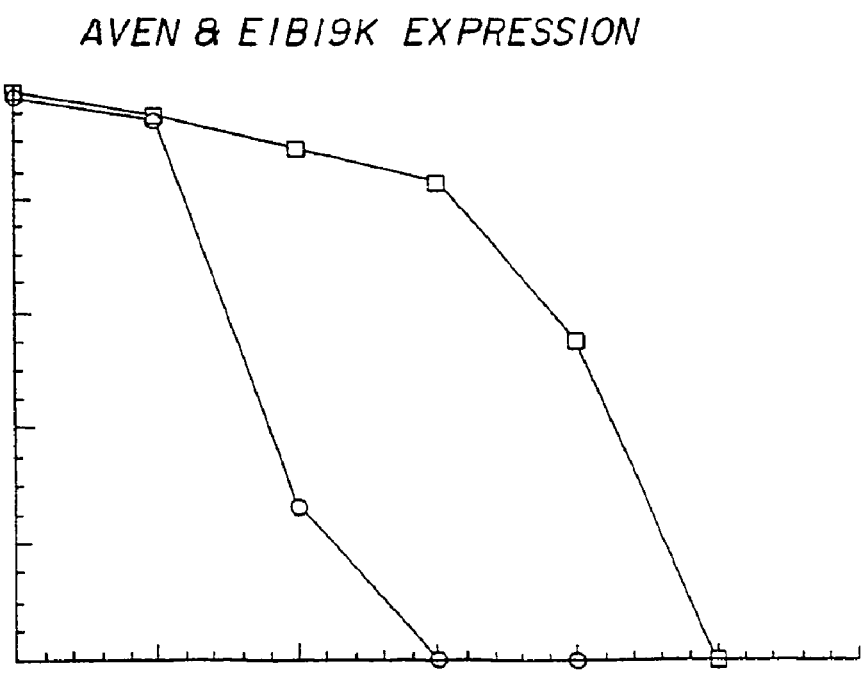
Figure 21:
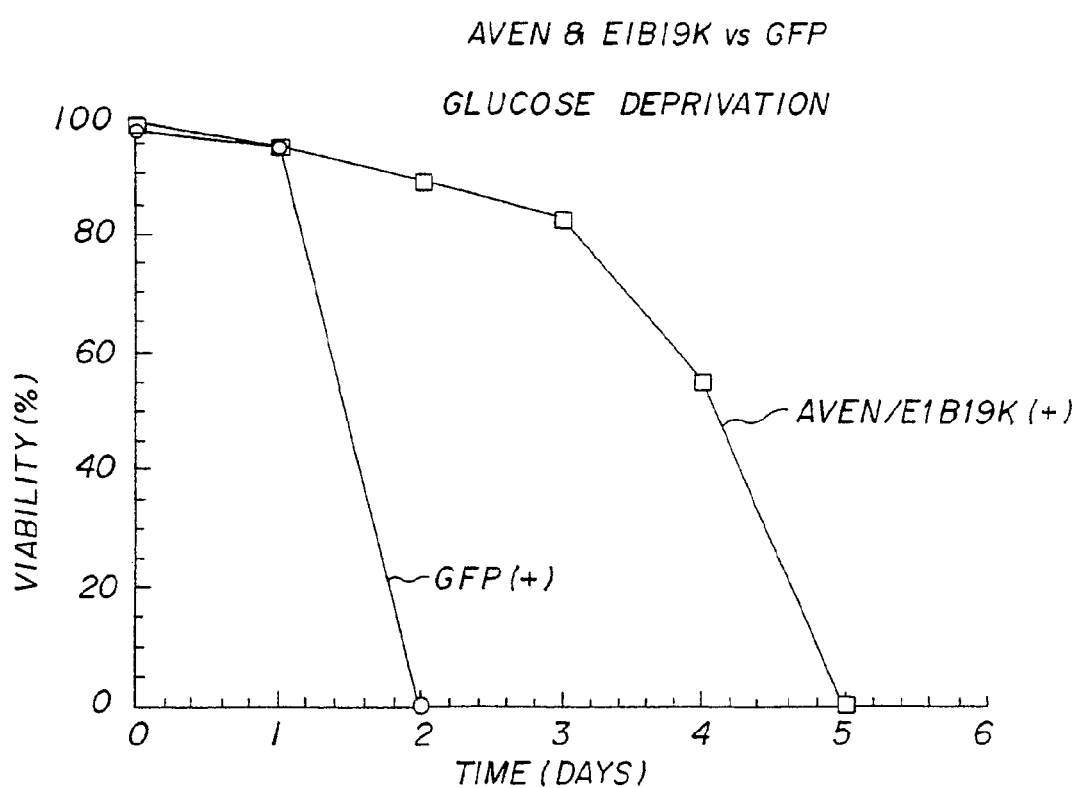

FIGS. 19, 20 and 21 respectively contain the results of experiments wherein the expression of Aven, Aven+E1B19K, and Aven+E1B19K vs. GFP are compared after induction with ponasterone A.

These results provide further evidence that Aven and E1B-19K are stably expressed after induction, with ponasterone A, that Aven alone provided little protection against apoptosis initiated by glucose deprivation, but that co-expression of Aven significantly enhanced E1B-19K protection against apoptosis initiated by glucose deprivation.

Example 13

Results with IDEC-131 Anti-Apoptotic Cell Line (14C6)

In this example, an IDEC-131 expressing CHO cell line (single cell isolate) is contacted with 500 nM methotrexate and transfected with pVgRXR Vector (Invitrogen vector) that constitutively expresses steroid receptor heterodimer to produce the 5C11 which is cultured under Zeocin resistance conditions.

Figure 22:
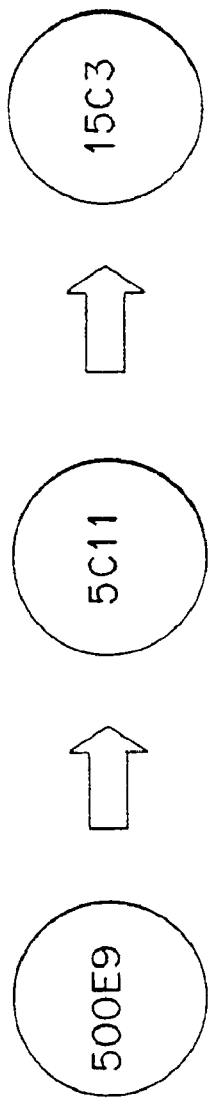
FIG. 22 depicts schematically the production of a CHO cell line that expresses IDEC-131 and the subject inducible expression vector containing anti-apoptotic genes.
Figure 25:
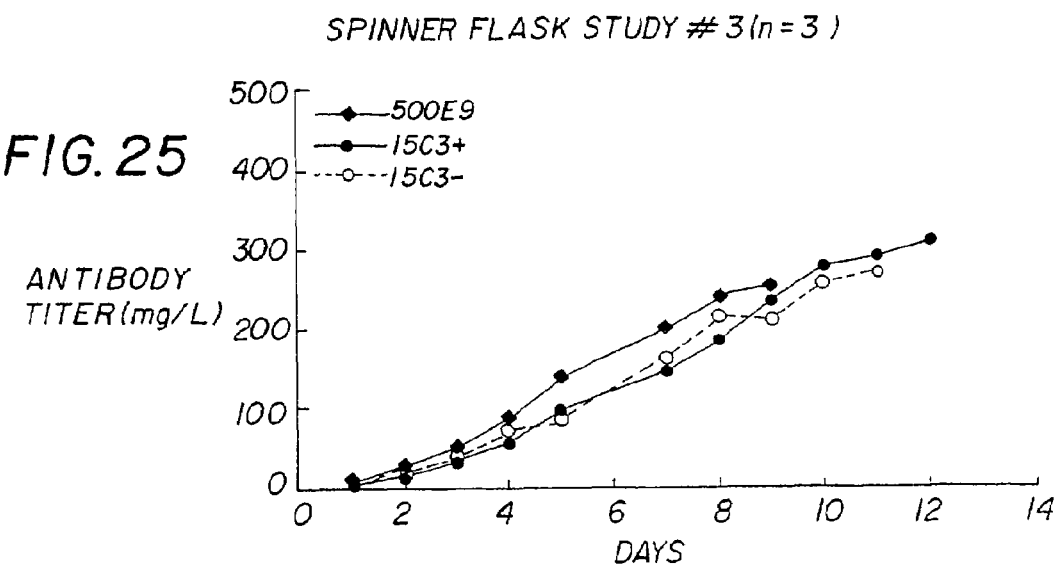
Figure 26:
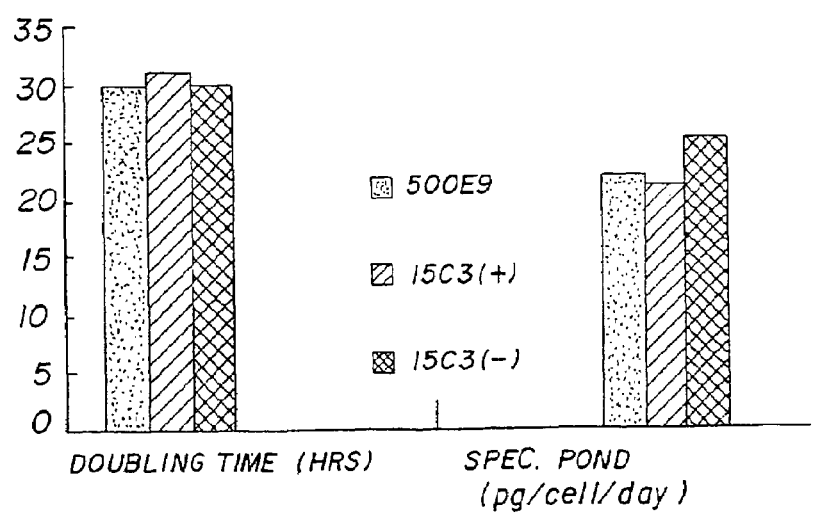

These cells are then transfected with the same inducible expression vector modified to certain anti-apoptotic genes (Modified Invitrogen vector contains Aven+E1B-19K genes), and the cells induced with ponasterone A and the transfected cells cultured under Zeocin/puromycin resistance conditions (These experiments are shown schematically in FIG. 22).

Cell lines were then compared to the original 500 E9 cell line based on criteria including growth rate, specific productivity (pg/cell/day), inducible protein expression (by western blot), and antibody titer (ELISA/HPLC).

In these experiments, 14 cell lines were evaluated, expressing E1B-19K and expressing both Aven and E1B19K. Three experiments were conducted at 100 mL volume, 1×duplicate, 2×triplicate, under induced and non-induced conditions.

The results of these experiments are contained in FIGS. 22-26. The results contained therein shown that the expression of E1B19K prolonged cell culture duration (w/wo induction), but had a demonstrable effect on cell growth and did not enhance antibody production.

Figure 27A:
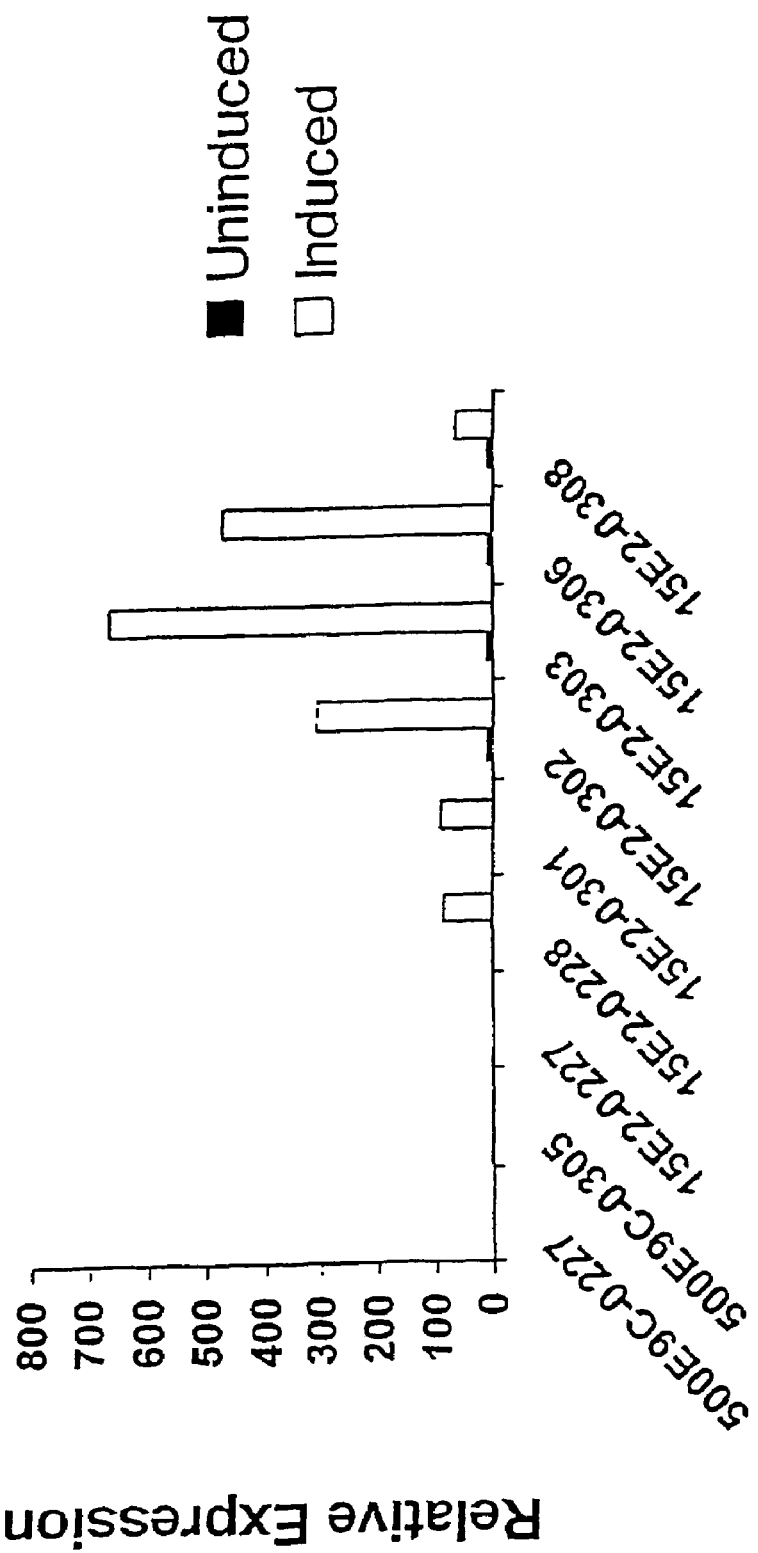
Figure 29:
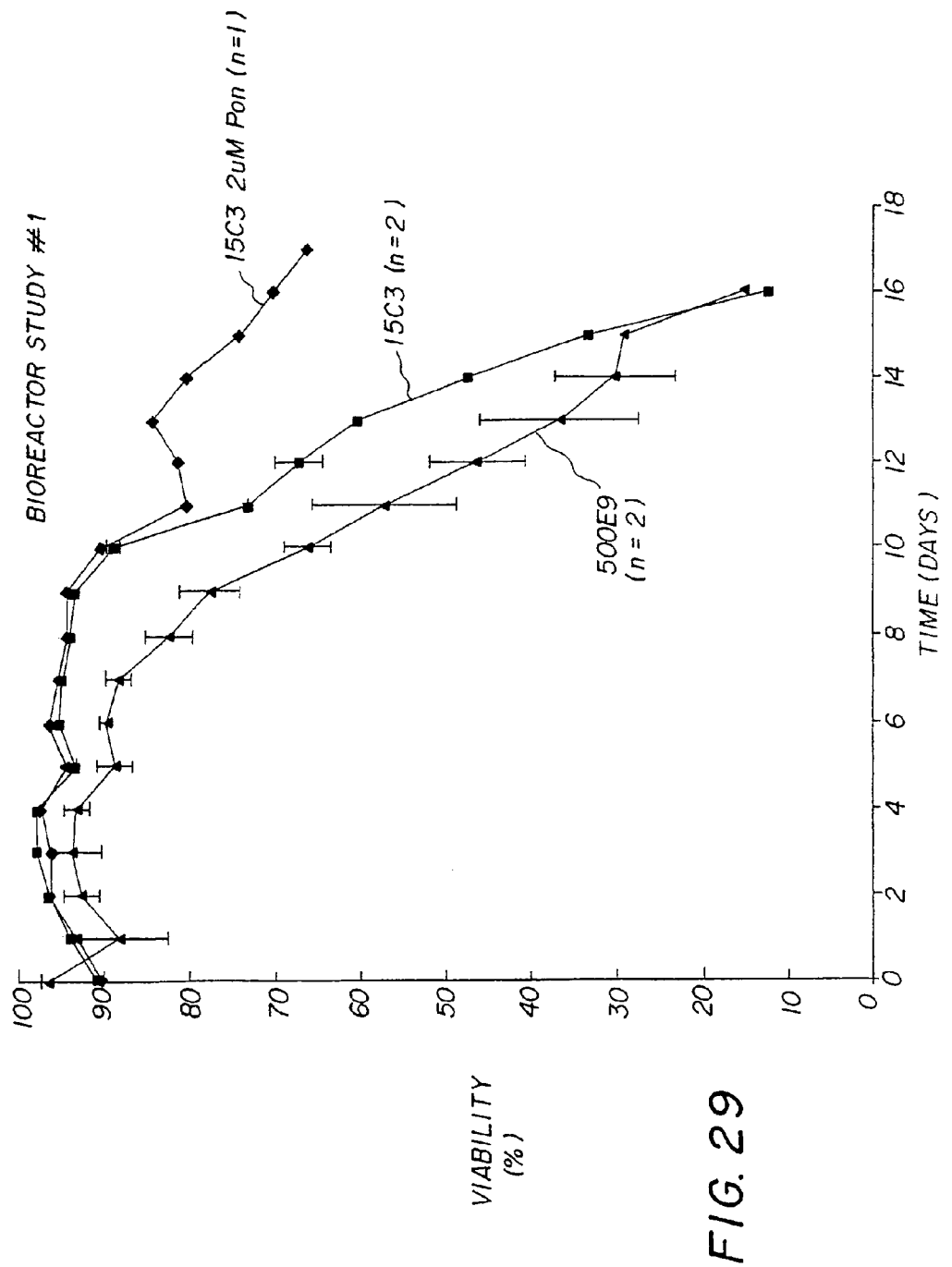
Figure 30:
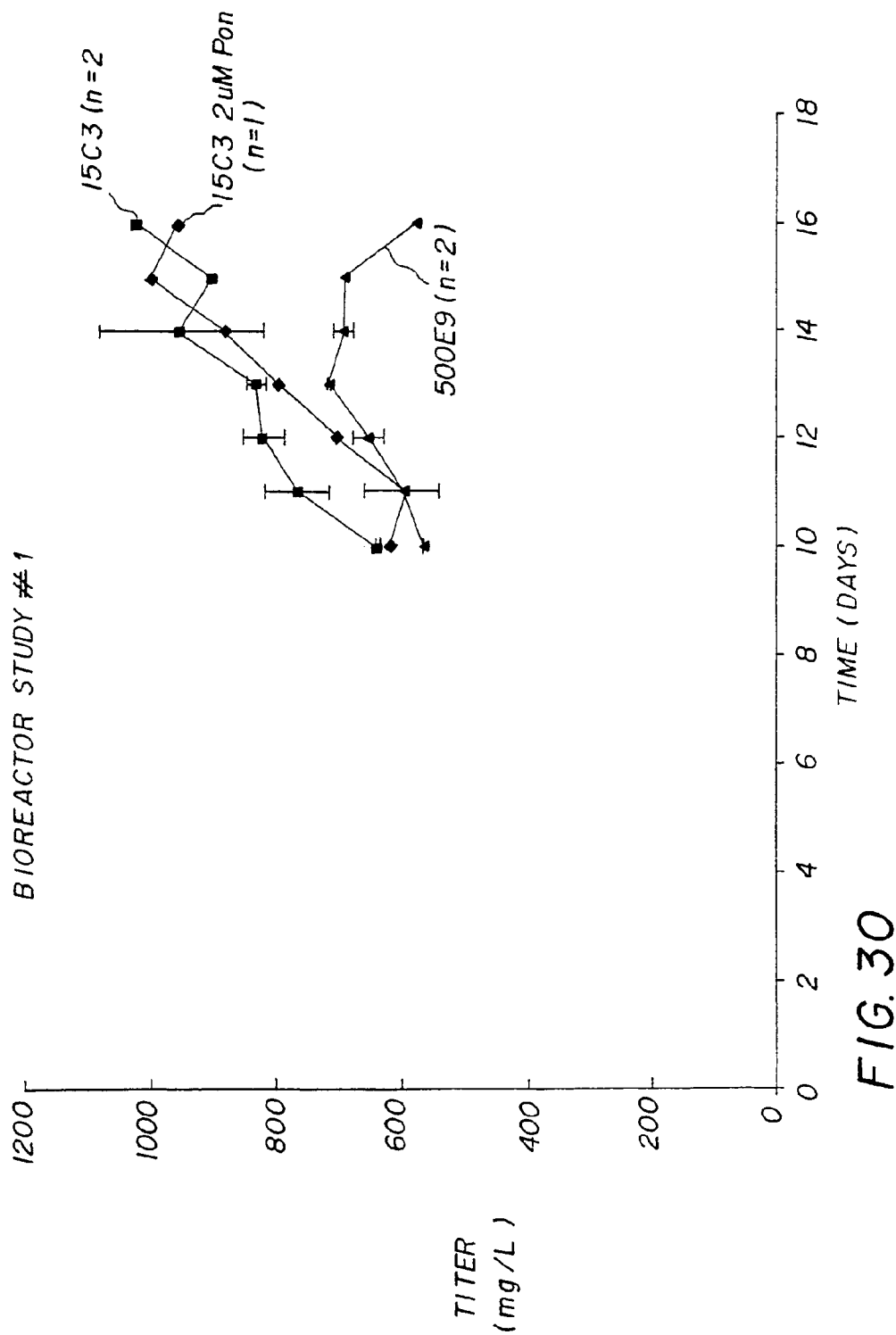
Figure 31:
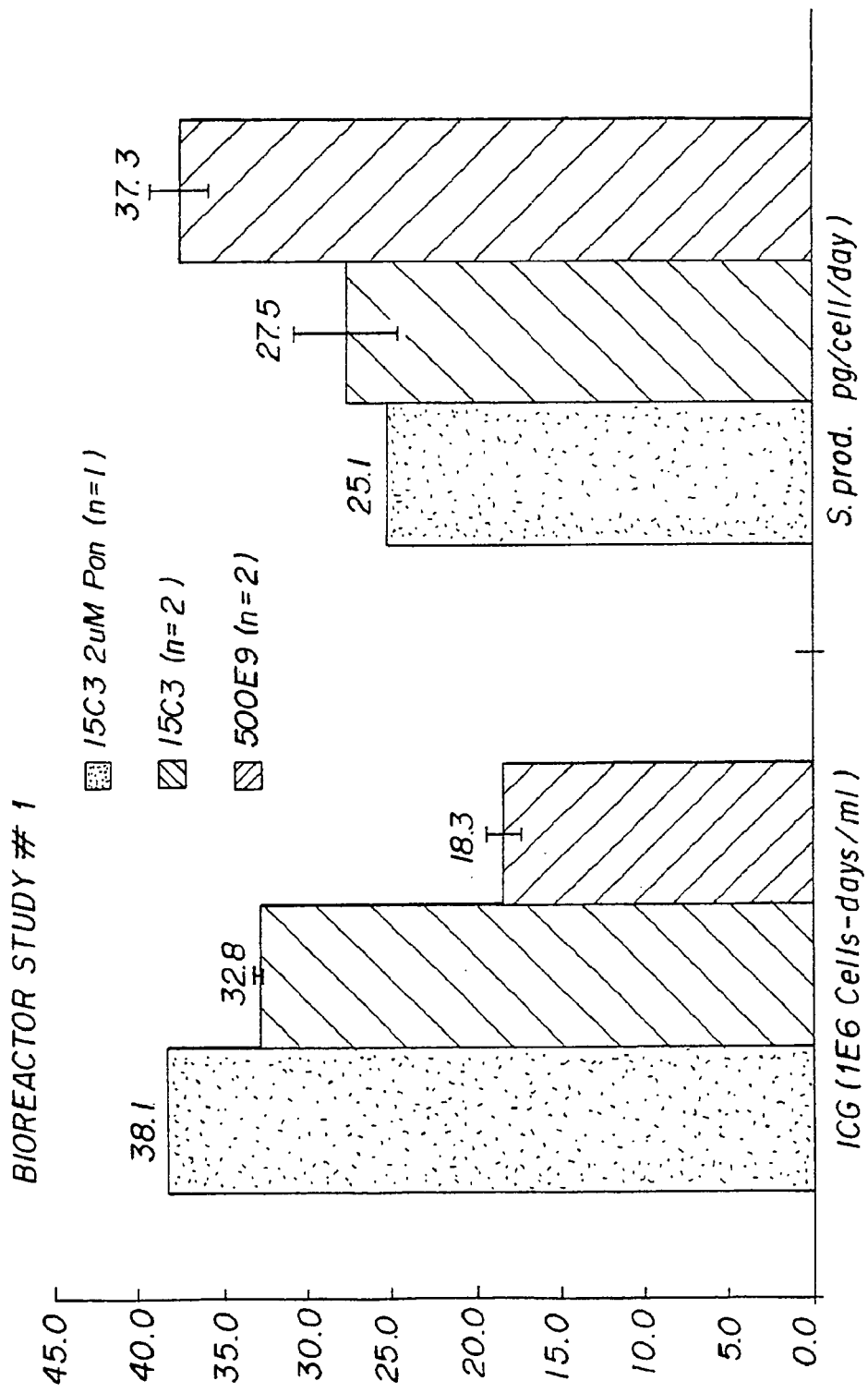
Figure 32:
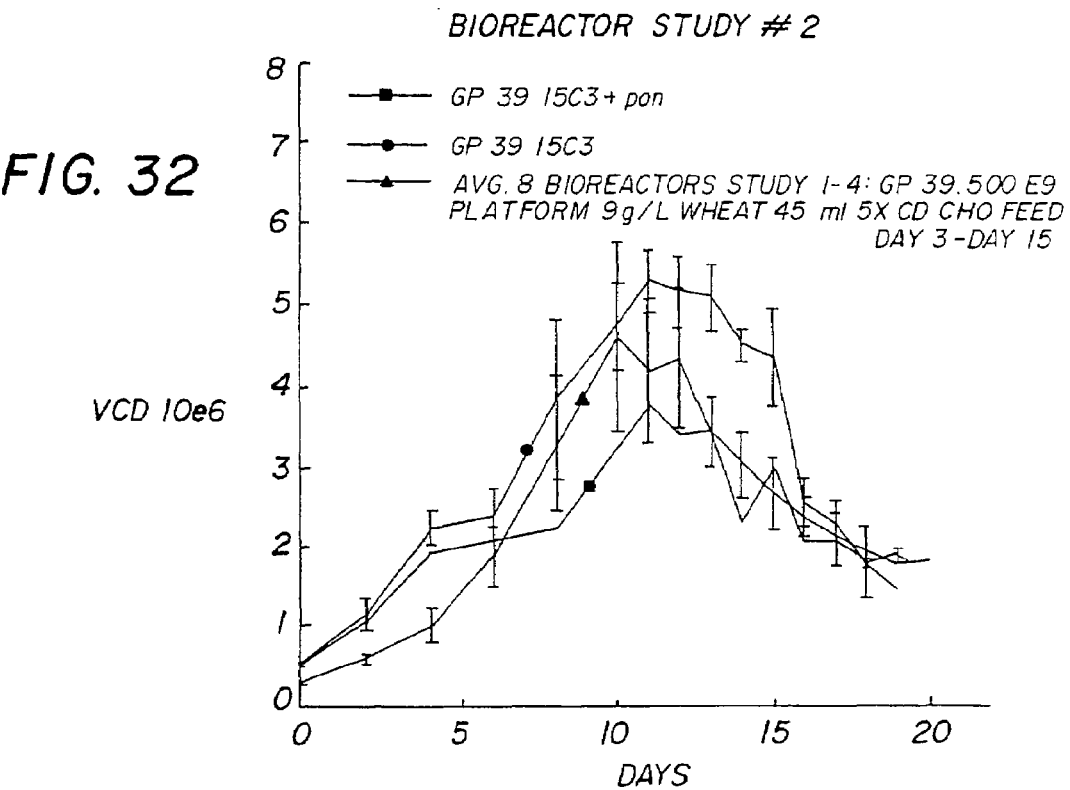
FIGS. 32-34 contain the results of bioreactor study #2.
Figure 33:
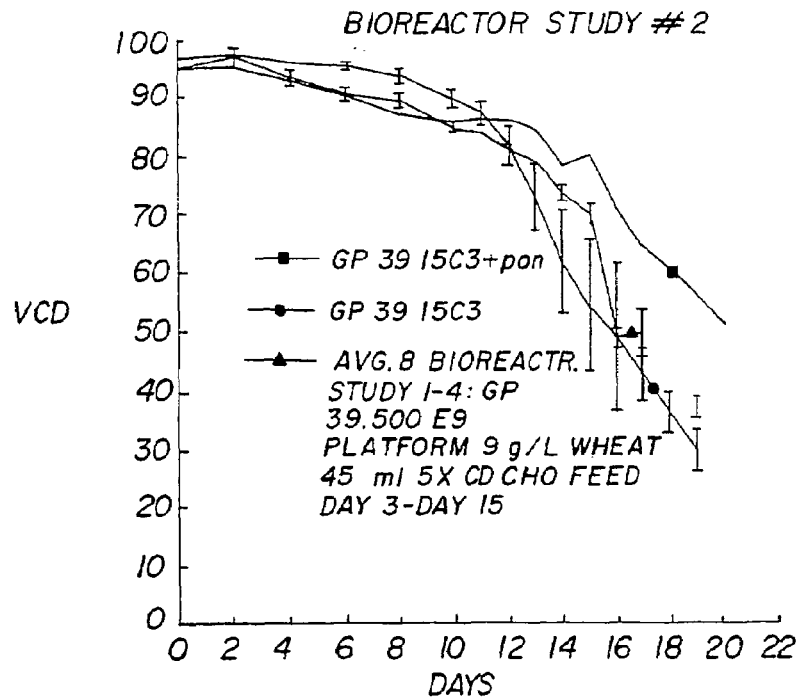
Figure 34:
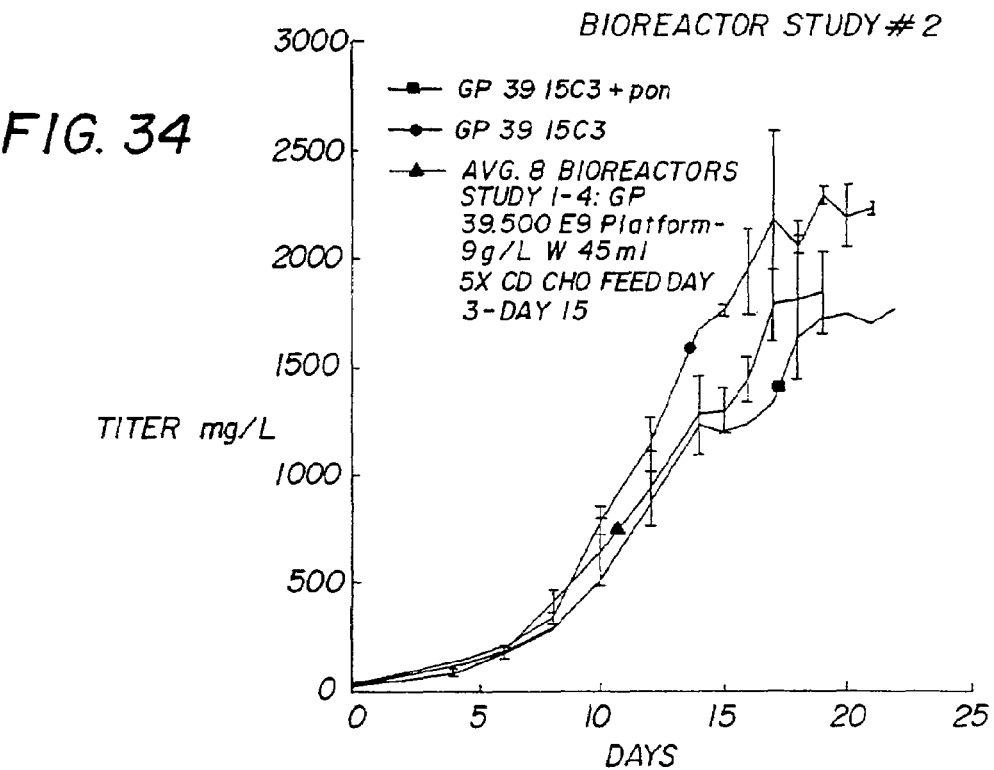
Figure 35:
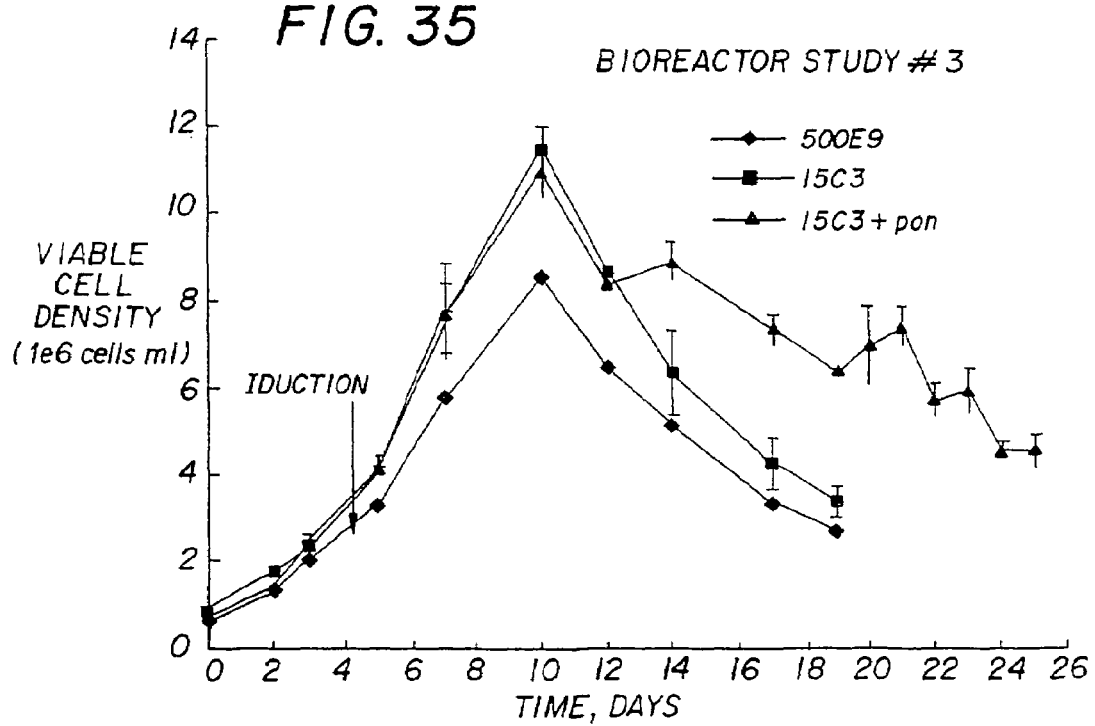

By contrast, cells which co-expressed Aven+E1B 19K had extended duration of cell cultures up to 3 days after induction, and significantly enhanced antibody titers (up to 20-30% relative to parent CHO cell line 500E9). These cells exhibit low-level constitutive expression of these anti-apoptotic genes (FIGS. 27A and 27B).

Example 14

Bioreactor Reactor Study #1

In these experiments, three cell lines (14C6, 15C3 and 15E2) were evaluated in 5 L bioreactors in a fed batch process. Three experiments were conducted using a single reactor, duplicate reactors under, induced vs. non-induced, conditions and using 3 different processes, and high density seeding.

The results of these bioreactors studies are contained in FIGS. 28-31. The results of this study show that both the induced and non-induced 15C3 cell line had higher cell viability, viable cell density and titer than 500E9.

The experimental results further indicate that the specific productivity of 15C3 was higher than 14C6, but both were lower than the 500 E9 cell line. It was also observed that ponasterone induction did not improve antibody titers of the 15C3 cell line.

Example 15

Bioreactor Study #2

In these experiments the 15C3 antibody producing cell line was cultured under induced early log phase conditions again using ponasterone A as the inducing agent. These results are contained in FIGS. 32-37 and show that non-induced cultures produced higher viabilities, cell densities, and titers than the 500E9 cell line.

Specifically, in non-induced cultures antibody titers were 20-30% higher than in the 500E9 cell line. It was also observed that induction increased culture longevity but did not improve antibody titers and that specific productivity was lower than in the 500E9 cell line.

Example 16

Bioreactor Study #3

A third bioreactor study was conducted wherein the same 500E9 and 15C3 cell line were seeded at high density in 100% fresh medium, and induced at mid-log phase. The results of this study are contained in FIGS. 35-37. These results show that 15C3 cultures produced higher cell derivatives and titers than 500E9 with non-induced culture titers being 20-30% higher than for 500E9. Induction again increased culture longevity but did not improve antibody titers. The results also show that specific productivity of 15C3 was lower than 500E9.

Thus, in conclusion the results of the experiments described in the previous examples demonstrate that the CHO DG44 cell line undergoes apoptotic cell death when subjected to extended culture and glucose deprivation, and that cell lines which express the anti-apoptotic genes alone or in combination exhibit an increase in cell viability and productivity in spinner flask and bioreactor cultures for CHO cell lines that express both of the tested anti-apoptotic genes (Aven and E1B-19K genes).

These results indicate that the expression of one or more anti-apoptotic genes, preferably under regulation of an inducible promoter as in the Ecdysone inducible expression system provides a viable means of enhancing the specific productivity of cell cultures, e.g., mammalian cell cultures producing a desired recombinant protein.

All patent and non-patent references cited this application are incorporated by reference in their entirety herein.

While the findings detailed description has described several embodiments of the present invention, it is to be understood that the above description is illustrative only and not limiting of the disclosed invention. The invention is to be limited only by the claims which follow.

The invention claimed is:

1. A method for preventing or delaying programmed cell death in an isolated recombinant cell, the method comprising expressing two or more anti-apoptotic polypeptides in the cell such that programmed cell death in the cell is prevented or delayed, wherein the two or more anti-apoptotic polypeptides comprise E1B-19K and Aven, and wherein the cell further comprises heterologous polynucleotides encoding E1B-19K and Aven.

2. The method of claim 1, wherein expression of two or more anti-apoptotic polypeptides is controlled by at least one inducible heterologous promoter operably linked to a the heterologous polynucleotides encoding E1B-19K and Aven.

3. The method of claim 2, wherein the inducible heterologous promoter is inducible by a steroid.

4. The method of claim 2, wherein the inducible heterologous promoter is an ecdysone promoter.

5. The method of claim 2, wherein the isolated recombinant cell further comprises a screenable or selectable marker operably linked to the at least one inducible heterologous promoter.

6. The method of claim 5, wherein the screenable or selectable marker is green fluorescence protein (GFP) or enhanced green fluorescence protein (EGF).

7. The method of claim 1, wherein the anti-apoptotic polypeptides are encoded by genes in eukaryotic cells or viruses.

8. The method of claim 1, wherein the isolated recombinant cell is a mammalian cell.

9. The method of claim 8, wherein the isolated recombinant cell is selected from the group consisting of human cells, murine cells, and rodent cells.

10. The method of claim 8, wherein the isolated recombinant cell is a CHO cell.

11. The method of claim 8, wherein the isolated recombinant cell is a BHK cell.

12. The method of claim 1, wherein the isolated recombinant cell is in a large scale bioreactor or culture device of a commercial production.

13. A method of increasing production of a cell-related product by an isolated recombinant cell, the method comprising expressing two or more anti-apoptotic polypeptides in the cell such that production of the cell-related product by the cell is increased, wherein the two or more anti-apoptotic polypeptides comprise E1B-19K and Aven, and wherein the cell further comprises heterologous polynucleotides encoding E1B-19K and Aven.

14. The method of claim 13, wherein the cell-related product is selected from the group consisting of cell-secretion factors.

15. The method of claim 13, wherein expression of two or more anti-apoptotic polypeptides is controlled by at least one inducible heterologous promoter operably linked to the heterologous polynucleotides encoding E1B-19K and Aven.

16. The method of claim 15, wherein the inducible heterologous promoter is inducible by a steroid.

17. The method of claim 15, wherein the inducible heterologous promoter is an ecdysone promoter.

18. The method of claim 15, wherein the isolated recombinant cell further comprises a screenable or selectable marker operably linked to the at least one inducible heterologous promoter.

19. The method of claim 18, wherein the screenable or selectable marker is green fluorescence protein (GFP) or enhanced green fluorescence protein (EGF).

20. The method of claim 13, wherein the anti-apoptotic polypeptides are encoded by genes in eukaryotic cells or viruses.

21. The method of claim 13, wherein the isolated recombinant cell is a mammalian cell.

22. The method of claim 21, wherein the isolated recombinant cell is selected from the group consisting of human cells, murine cells, and rodent cells.

23. The method of claim 21, wherein the isolated recombinant cell is a CHO cell.

24. The method of claim 21, wherein the isolated recombinant cell is a BHK cell.

25. The method of claim 13, wherein the isolated recombinant cell is in a large scale bioreactor or culture device of a commercial production.

26. A method of increasing production of an isolated recombinant cell product, the method comprising expressing two or more anti-apoptotic polypeptides in the cell such that production of the isolated recombinant cell product is increased, wherein the two or more anti-apoptotic polypeptides comprise E1B-19K and Aven, and wherein the cell further comprises heterologous polynucleotides encoding E1B-19K and Aven.

27. An isolated recombinant cell useful for producing cell-related product expressing two or more anti-apoptotic polypeptides, wherein the two or more anti-apoptotic polypeptides comprise E1B-19K and Aven, and wherein the cell further comprises heterologous polynucleotides encoding E1B-19K and Aven.

28. The isolated recombinant cell of claim 27, wherein the anti-apoptotic polypeptides are encoded by genes in eukaryotic cells or viruses.

29. The isolated recombinant cell of claim 27, wherein the cell-related product is selected from the group consisting of cell-secretion factors.

30. The isolated recombinant cell of claim 27, wherein expression of two or more anti-apoptotic polypeptides is controlled by at least one inducible heterologous promoter operably linked to the heterologous polynucleotides encoding E1B-19K and Aven.

31. The isolated recombinant cell of claim 30, wherein the inducible heterologous promoter is inducible by a steroid.

32. The isolated recombinant cell of claim 30, wherein the inducible heterologous promoter is an ecdysone promoter.

33. The isolated recombinant cell of claim 30, wherein the isolated recombinant cell further comprises a screenable or selectable marker operably linked to the at least one inducible heterologous promoter.

34. The isolated recombinant cell of claim 33, wherein the screenable or selectable marker is green fluorescence protein (GFP) or enhanced green fluorescence protein (EGF).

35. The isolated recombinant cell of claim 27, wherein the isolated recombinant cell is a mammalian cell.

36. The isolated recombinant cell of claim 27, wherein the isolated recombinant cell is selected from the group consisting of human cells, murine cells, and rodent cells.

37. The isolated recombinant cell of claim 35, wherein the isolated recombinant cell is a CHO cell.

38. The isolated recombinant cell of claim 27, wherein the isolated recombinant cell is a BHK cell.

39. The isolated recombinant cell of claim 27, wherein the cell produces cell-related product in a large scale bioreactor or culture device of commercial production.

40. A population of isolated recombinant cells useful for producing one or more biological functions of the cells expressing two or more anti-apoptotic polypeptides, wherein the two or more anti-apoptotic polypeptides comprise E1B-19K and Avena and wherein the cell further comprises heterologous polynucleotides encoding E1B-19K and Aven.

41. An isolated recombinant cell with prevented or delayed programmed cell death, prepared by the method of claim 1.

42. The method of claim 1, wherein the isolated recombinant cell is derived from a single cell.

43. The method of claim 13, wherein the isolated recombinant cell is derived from a single cell.

44. The method of claim 26, wherein the isolated recombinant cell is derived from a single cell.

45. The isolated recombinant cell of claim 27, wherein the isolated recombinant cell is derived from a single cell.

46. The isolated recombinant cell population of claim 40, wherein the isolated recombinant cell population is derived from a single cell.

* * * * *

UNITED STATES PATENT AND TRADEMARK OFFICE
CERTIFICATE OF CORRECTION

| | | |
|---|---|---|
| PATENT NO. | : 7,604,989 B2 | Page 1 of 1 |
| APPLICATION NO. | : 10/191052 | |
| DATED | : October 20, 2009 | |
| INVENTOR(S) | : Reff et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1060 days.

Signed and Sealed this

Fifth Day of October, 2010

David J. Kappos
*Director of the United States Patent and Trademark Office*

SEQUENCE LISTING

```
<160> NUMBER OF SEQ ID NOS: 6

<210> SEQ ID NO 1
<211> LENGTH: 1089
<212> TYPE: DNA
<213> ORGANISM: Artificial Sequence
<220> FEATURE:
<223> OTHER INFORMATION: Description of Artificial Sequence: Aven
      nucleotide sequence

<400> SEQUENCE: 1
atgaacgcgg agcgaggagc tcggggaggc cgtgggcggc ggccaggccg cggccggcct      60
ggcggagatc gccacagcga gcggcccgga gccgcagcgg cggtagccag aggcggcggc     120
ggaggcggcg gcggggacgg aggcggacgc cggggccgtg gccgtggccg gggcttccgc     180
ggcgctcgcg gaggccgagg aggaggaggc gccccgcgag gcagccgccg ggagccggga     240
ggctggggcg caggggccag cgcgccggtt gaagatgaca gcgatgcaga gacctatgga     300
gaagagaatg atgaacaggg aaattattct aaaagaaaga ttgtctctaa ctgggatcga     360
tatcaagata ttgaaaaaga ggtcaataat gaaagtggag agtcacagag gggaacagat     420
ttcagtgtcc tccttagctc tgcagggac tcattctcac agttccggtt tgctgaggag      480
aaagaatggg atagtgaagc ttcttgtcca aaacagaatt cagcatttta tgtggatagt     540
gagttattgg ttcgagccct tcaagagctg cctctctgcc tccgactcaa cgttgctgcc     600
gaactggtcc agggtacagt tcctttagag gttcctcagg tgaaaccaaa gagaactgat     660
gatggcaagg gattagggat gcagttaaag gggcccttgg ggcctggagg aagggggccc     720
atctttgagc tgaaatctgt ggctgctggc tgccctgtgt tgctgggcaa agacaaccca     780
agcccgggtc cttcaaggga ttctcagaaa cccacttccc cactgcagtc agcaggagac     840
catttggaag aagaactaga tctgttgctt aatttagatg cacctataaa agagggagat     900
aacatcttac cagatcagac gtctcaggac ctgaaatcca aggaagatgg ggaggtggtc     960
caagaggaag aagtttgtgc aaaaccatct gtgactgaag aaaaaaacat ggaacctgag    1020
caaccaagta cctccaaaaa tgttaccgag gaagagctgg aagactggtt ggacagcatg    1080
atttcctaa                                                            1089

<210> SEQ ID NO 2
<211> LENGTH: 362
<212> TYPE: PRT
<213> ORGANISM: Artificial Sequence
<220> FEATURE:
<223> OTHER INFORMATION: Description of Artificial Sequence: Aven
      protein sequence

<400> SEQUENCE: 2

Met Asn Ala Glu Arg Gly Ala Arg Gly Gly Arg Gly Arg Arg Pro Gly
  1               5                  10                  15

Arg Gly Arg Pro Gly Gly Asp Arg His Ser Glu Arg Pro Gly Ala Ala
                 20                  25                  30

Ala Ala Val Ala Arg Gly Gly Gly Gly Gly Gly Gly Asp Gly Gly
             35                  40                  45
```

```
Gly Arg Arg Gly Arg Gly Arg Gly Phe Arg Gly Ala Arg Gly
        50                  55                  60
Gly Arg Gly Gly Gly Ala Pro Arg Gly Ser Arg Glu Pro Gly
65                  70                  75                  80
Gly Trp Gly Ala Gly Ala Ser Ala Pro Val Glu Asp Ser Asp Ala
                85                  90                  95
Glu Thr Tyr Gly Glu Glu Asn Asp Glu Gln Gly Asn Tyr Ser Lys Arg
            100                 105                 110
Lys Ile Val Ser Asn Trp Asp Arg Tyr Gln Asp Ile Glu Lys Glu Val
            115                 120                 125
Asn Asn Glu Ser Gly Glu Ser Gln Arg Gly Thr Asp Phe Ser Val Leu
130                 135                 140
Leu Ser Ser Ala Gly Asp Ser Phe Ser Gln Phe Arg Phe Ala Glu Glu
145                 150                 155                 160
Lys Glu Trp Asp Ser Glu Ala Ser Cys Pro Lys Gln Asn Ser Ala Phe
                165                 170                 175
Tyr Val Asp Ser Glu Leu Leu Val Arg Ala Leu Gln Glu Leu Pro Leu
            180                 185                 190
Cys Leu Arg Leu Asn Val Ala Ala Glu Leu Val Gln Gly Thr Val Pro
        195                 200                 205
Leu Glu Val Pro Gln Val Lys Pro Lys Arg Thr Asp Asp Gly Lys Gly
    210                 215                 220
Leu Gly Met Gln Leu Lys Gly Pro Leu Gly Pro Gly Gly Arg Gly Pro
225                 230                 235                 240
Ile Phe Glu Leu Lys Ser Val Ala Ala Gly Cys Pro Val Leu Leu Gly
                245                 250                 255
Lys Asp Asn Pro Ser Pro Gly Pro Ser Arg Asp Ser Gln Lys Pro Thr
            260                 265                 270
Ser Pro Leu Gln Ser Ala Gly Asp His Leu Glu Glu Leu Asp Leu
        275                 280                 285
Leu Leu Asn Leu Asp Ala Pro Ile Lys Glu Gly Asp Asn Ile Leu Pro
    290                 295                 300
Asp Gln Thr Ser Gln Asp Leu Lys Ser Lys Glu Asp Gly Glu Val Val
305                 310                 315                 320
Gln Glu Glu Glu Val Cys Ala Lys Pro Ser Val Thr Glu Glu Lys Asn
                325                 330                 335
Met Glu Pro Glu Gln Pro Ser Thr Ser Lys Asn Val Thr Glu Glu Glu
            340                 345                 350
Leu Glu Asp Trp Leu Asp Ser Met Ile Ser
        355                 360

<210> SEQ ID NO 3
<211> LENGTH: 531
<212> TYPE: DNA
<213> ORGANISM: Artificial Sequence
<220> FEATURE:
<223> OTHER INFORMATION: Description of Artificial Sequence: E1B-19K
      (type 5) nucleotide sequence

<400> SEQUENCE: 3
atggaggctt gggagtgttt ggaagatttt tctgctgtgc gtaacttgct ggaacagagc    60
tctaacagta cctcttggtt ttggaggttt ctgtggggct catcccaggc aaagttagtc   120
tgcagaatta aggaggatta caagtgggaa tttgaagagc ttttgaaatc ctgtggtgag   180
ctgtttgatt ctttgaatct gggtcaccag gcgcttttcc aagagaaggt catcaagact   240
```

```
ttggattttt ccacaccggg gcgcgctgcg gctgctgttg cttttttgag ttttataaag    300
gataaatgga gcgaagaaac ccatctgagc ggggggtacc tgctggattt tctggccatg    360
catctgtgga gagcggttgt gagacacaag aatcgcctgc tactgttgtc ttccgtccgc    420
ccggcgataa taccgacgga ggagcagcag cagcagcagg aggaagccag gcggcggcgg    480
caggagcaga gcccatggaa cccgagagcc ggcctggacc ctcgggaatg a             531
```

<210> SEQ ID NO 4
<211> LENGTH: 176
<212> TYPE: PRT
<213> ORGANISM: Artificial Sequence
<220> FEATURE:
<223> OTHER INFORMATION: Description of Artificial Sequence: E1B-19K
      (type 2) protein sequence

<400> SEQUENCE: 4

```
Met Glu Ala Trp Glu Cys Leu Glu Asp Phe Ser Ala Val Arg Asn Leu
 1               5                  10                  15

Leu Glu Gln Ser Ser Asn Ser Thr Ser Trp Phe Trp Arg Phe Leu Trp
                20                  25                  30

Gly Ser Ser Gln Ala Lys Leu Val Cys Arg Ile Lys Glu Asp Tyr Lys
            35                  40                  45

Trp Glu Phe Glu Glu Leu Leu Lys Ser Cys Gly Glu Leu Phe Asp Ser
        50                  55                  60

Leu Asn Leu Gly His Gln Ala Leu Phe Gln Glu Lys Val Ile Lys Thr
65                  70                  75                  80

Leu Asp Phe Ser Thr Pro Gly Arg Ala Ala Ala Val Ala Phe Leu
                85                  90                  95

Ser Phe Ile Lys Asp Lys Trp Ser Glu Glu Thr His Leu Ser Gly Gly
                100                 105                 110

Tyr Leu Leu Asp Phe Leu Ala Met His Leu Trp Arg Ala Val Val Arg
            115                 120                 125

His Lys Asn Arg Leu Leu Leu Leu Ser Ser Val Arg Pro Ala Ile Ile
        130                 135                 140

Pro Thr Glu Glu Gln Gln Gln Gln Glu Glu Ala Arg Arg Arg Arg
145                 150                 155                 160

Gln Glu Gln Ser Pro Trp Asn Pro Arg Ala Gly Leu Asp Pro Arg Glu
                165                 170                 175
```

<210> SEQ ID NO 5
<211> LENGTH: 528
<212> TYPE: DNA
<213> ORGANISM: Artificial Sequence
<220> FEATURE:
<223> OTHER INFORMATION: Description of Artificial Sequence: E1B-19K
      (type 2) nucleotide sequence

<400> SEQUENCE: 5

```
atggaggctt gggagtgttt ggaagatttt tctgctgtgc gtaacttgct ggaacagagc    60
tctaacagta cctcttggtt ttggaggttt ctgtggggct catcccaggc aaagttagtc   120
tgcagaatta aggaggatta caagtgggaa tttgaagagc ttttgaaatc ctgtggtgag   180
ctgtttgatt ctttgaatct gggtcaccag gcgcttttcc aagagaaggt catcaagact   240
ttggattttt ccacaccggg gcgcgctgcg gctgctgttg cttttttgag ttttataaag   300
gataaatgga gtgaagaaac ccatctgagc ggggggtacc tgctggattt tctggccatg   360
catctgtgga gagcggtggt gagacacaag aatcgcctgc tactgttgtc ttccgtccgc   420
```

-continued

```
ccggcaataa taccgacgga ggagcaacag caggaggaag ccaggcggcg gcggcggcag      480
gagcagagcc catggaaccc gagagccggc ctggaccctc gggaatga                  528
```

<210> SEQ ID NO 6
<211> LENGTH: 175
<212> TYPE: PRT
<213> ORGANISM: Artificial Sequence
<220> FEATURE:
<223> OTHER INFORMATION: Description of Artificial Sequence: E1B-19K
      (type 2) protein sequence

<400> SEQUENCE: 6

```
Met Glu Ala Trp Glu Cys Leu Glu Asp Phe Ser Ala Val Arg Asn Leu
 1               5                  10                  15

Leu Glu Gln Ser Ser Asn Ser Thr Ser Trp Phe Trp Arg Phe Leu Trp
            20                  25                  30

Gly Ser Ser Gln Ala Lys Leu Val Cys Arg Ile Lys Glu Asp Tyr Lys
        35                  40                  45

Trp Glu Phe Glu Glu Leu Leu Lys Ser Cys Gly Glu Leu Phe Asp Ser
    50                  55                  60

Leu Asn Leu Gly His Gln Ala Leu Phe Gln Glu Lys Val Ile Lys Thr
65                  70                  75                  80

Leu Asp Phe Ser Thr Pro Gly Arg Ala Ala Ala Ala Val Ala Phe Leu
                85                  90                  95

Ser Phe Ile Lys Asp Lys Trp Ser Glu Glu Thr His Leu Ser Gly Gly
            100                 105                 110

Tyr Leu Leu Asp Phe Leu Ala Met His Leu Trp Arg Ala Val Val Arg
        115                 120                 125

His Lys Asn Arg Leu Leu Leu Ser Ser Val Arg Pro Ala Ile Ile
    130                 135                 140

Pro Thr Glu Glu Gln Gln Gln Glu Glu Ala Arg Arg Arg Arg Arg Gln
145                 150                 155                 160

Glu Gln Ser Pro Trp Asn Pro Arg Ala Gly Leu Asp Pro Arg Glu
                165                 170                 175
```